US009988367B2

(12) United States Patent
Collin et al.

(10) Patent No.: US 9,988,367 B2
(45) Date of Patent: Jun. 5, 2018

(54) AMIDE-SUBSTITUTED PYRIDINYLTRIAZOLE DERIVATIVES AND USES THEREOF

(71) Applicant: BAYER PHARMA AKTIENGESELLSCHAFT, Berlin (DE)

(72) Inventors: Marie-Pierre Collin, Wuppertal (DE); Peter Kolkhof, Wuppertal (DE); Thomas Neubauer, Wuppertal (DE); Chantal Fürstner, Mülheim/Ruhr (DE); Elisabeth Pook, Wuppertal (DE); Matthias Beat Wittwer, Wuppertal (DE); Klemens Lustig, Wuppertal (DE); Anja Buchmüller, Essen (DE); Hanna Tinel, Wuppertal (DE); Karoline Dröbner, Wuppertal (DE); Thomas Mondritzki, Velbert (DE); Heiko Schirmer, Solingen (DE); Axel Kretschmer, Wuppertal (DE); Carsten Schmeck, Mülheim (DE); Pierre Wasnaire, Düsseldorf (DE); Hana Cernecka, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days. days.

(21) Appl. No.: 15/581,064

(22) Filed: Apr. 28, 2017

(65) Prior Publication Data
US 2017/0320854 A1 Nov. 9, 2017

(30) Foreign Application Priority Data

May 3, 2016 (EP) .................................... 16168165

(51) Int. Cl.
*A61K 31/4439* (2006.01)
*C07D 401/14* (2006.01)
*A61K 45/06* (2006.01)

(52) U.S. Cl.
CPC ........ *C07D 401/14* (2013.01); *A61K 31/4439* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,276,049 A | 1/1994 | Himmelsbach et al. |
| 5,281,614 A | 1/1994 | Ashton et al. |
| 5,326,776 A | 7/1994 | Winn et al. |
| 5,468,448 A | 11/1995 | Nicolson et al. |
| 5,585,394 A | 12/1996 | Di Malta et al. |
| 5,681,841 A | 10/1997 | Himmelsbach |
| 6,469,012 B1 | 10/2002 | Ellis et al. |
| 6,531,142 B1 | 3/2003 | Rabe et al. |
| 6,693,102 B2 | 2/2004 | Stasch et al. |
| 6,743,798 B1 | 6/2004 | Straub et al. |
| 6,746,989 B1 | 6/2004 | Muller et al. |
| 6,762,152 B1 | 7/2004 | Muller et al. |
| 6,833,364 B1 | 12/2004 | Straub et al. |
| 6,838,415 B1 | 1/2005 | Muller et al. |
| 6,864,287 B1 | 3/2005 | Alonso-Alija et al. |
| 6,924,251 B1 | 8/2005 | Schwarz et al. |
| 6,969,697 B2 | 11/2005 | Muller et al. |
| 7,080,644 B2 | 7/2006 | Gumaste |
| 7,642,275 B2 | 1/2010 | Bressi et al. |
| 7,674,825 B2 | 3/2010 | Alonso-Alija et al. |
| 8,084,481 B2 | 12/2011 | Meier et al. |
| 8,202,895 B2 | 6/2012 | Bruggemeier er al. |
| 2001/0020100 A1 | 9/2001 | Manning et al. |
| 2002/0045651 A1 | 4/2002 | Brenner et al. |
| 2002/0172644 A1 | 11/2002 | Haslwanter et al. |
| 2003/0161790 A1 | 8/2003 | Wahi et al. |
| 2004/0071757 A1 | 4/2004 | Rolf |
| 2004/0082798 A1 | 4/2004 | Alonso-Alija et al. |
| 2004/0176446 A1 | 9/2004 | Alonso-Alija et al. |
| 2006/0148779 A1 | 7/2006 | Bell et al. |
| 2007/0225333 A1 | 9/2007 | Bryans et al. |
| 2007/0281937 A1 | 12/2007 | Zelle et al. |
| 2008/0058314 A1 | 3/2008 | Alonso-Alija et al. |
| 2008/0139560 A1 | 6/2008 | Zelle et al. |
| 2011/0245308 A1 | 10/2011 | Bruggemeier et al. |
| 2012/0053218 A1 | 3/2012 | Bruggemeier et al. |
| 2012/0208852 A1 | 8/2012 | Furstner et al. |

(Continued)

FOREIGN PATENT DOCUMENTS

| | | |
|---|---|---|
| EP | 0051829 | 5/1982 |
| WO | 99/31099 | 6/1999 |

(Continued)

OTHER PUBLICATIONS

Arnswald & Neumann "Unconventional regiospecific syntheses of aromatic carbonamides and thiocarbonamides by means of tin-mediated friedel-crafts reaction" J. Org. Chem. 58:7022-7028 (1993).
Artursson & Karlsson "Correlation between oral drug absorption in humans and apparent drug permeability coefficients in human intestinal epithelial (CACO-2) cells" Biochem. Biophys. Res. Comm. 175:880-885 (1991).
Berge et al. "Pharmaceutical salts" J. Pharm. Sci. 66:1-19 (1977).
Bianchi & Häusermann "5-Oxo-1 H-4,5-dihydro-1,2,4-benzotriazepines. Chemical behavior towards alkylating, acidic and alkaline agents" J. Heterocyclic Chem. 16:1411-1416 (1979).
Bronson et al. "Discovery of the first antibacterial small molecule inhibitors of murB" Bioorg. Med. Chem. Lett. 13:873-875 (2003).
Chan et al. "Copper promoted C—N and C—O bond cross-coupling with phenyl and pyridylboronates" Tetrahedron Lett. 44:3863-3865 (2003).
Chang et al. "Triazolinones as nonpeptide angiotensin II antagonists. Synthesis and evaluation of potent 2,4,5-trisubstituted triazolinones" J. Med. Chem. 36:2558-2668 (1993).
Cheng & Prusoff "Relationship between the inhibition constant ($K_i$) and the concentration of inhibitor which causes 50 per cent inhibition ($I_{50}$) of an enzymatic reaction" Biochem. Pharmacol. 22:3099-3108 (1973).

(Continued)

*Primary Examiner* — Samantha L Shterengarts
(74) *Attorney, Agent, or Firm* — Nixon & Vanderhye PC

(57) ABSTRACT

The present invention relates to novel 5-(carboxamide)-1-pyridinyl-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

14 Claims, No Drawings

(56) References Cited

U.S. PATENT DOCUMENTS

| | | |
|---|---|---|
| 2012/0238607 A1 | 9/2012 | Bruggemeier et al. |
| 2013/0225646 A1 | 8/2013 | Furstner et al. |

FOREIGN PATENT DOCUMENTS

| | | |
|---|---|---|
| WO | 2000/006568 | 2/2000 |
| WO | 2000/006569 | 2/2000 |
| WO | 2000/059510 | 10/2000 |
| WO | 2001/000595 | 1/2001 |
| WO | 2001/019355 | 3/2001 |
| WO | 2001/019776 | 3/2001 |
| WO | 2001/019778 | 3/2001 |
| WO | 2001/019780 | 3/2001 |
| WO | 2002/042301 | 5/2002 |
| WO | 2002/066447 | 8/2002 |
| WO | 2002/070462 | 9/2002 |
| WO | 2002/070510 | 9/2002 |
| WO | 2003/095451 | 11/2003 |
| WO | 2005/006892 | 1/2005 |
| WO | 2005/063754 | 7/2005 |
| WO | 2005/105779 | 11/2005 |
| WO | 2006/117657 | 11/2006 |
| WO | 2010/105770 | 9/2010 |
| WO | 2011/104322 | 9/2011 |
| WO | 2011/147809 | 12/2011 |
| WO | 2012/004258 | 1/2012 |
| WO | 2012/028647 | 3/2012 |
| WO | 2012/059549 | 5/2012 |
| WO | 2013/138860 | 9/2013 |
| WO | 2016/071212 | 5/2016 |

OTHER PUBLICATIONS

Corey & Schmidt "Useful procedures for the oxidation of alcohols involving pyridinium dichromate in aprotic media" Tetrahedron Lett. 5:399-402 (1979).

De Luca et al. "Hyponatremia in patients with heart failure" Am. J. Cardiol. 96(suppl):19L-23L (2005).

Dobosz et al. "Synthesis and some pharmacological properties of 3-(4-phenyl-5-oxo-1,2,4-triazolin-1-ylmethyl)1,2,4-triazolin-5-thione derivatives" Acta Pol. Pharm. 59:281-290 (2002).

Dess "Readily accessible 12-I-5 oxidant for the conversion of primary and secondary alcohols to aldehydes and ketones" J. Org. Chem. 48:4155-4156 (1983).

Finley et al. "Arginine vasopressin antagonists for the treatment of heart failure and hyponatremia" Circulation 118:410-421 (2008).

Francis et al. "Comparison of neuroendocrine activation in patients with left ventricular dysfunction with and without congestive heart failure" Circulation 82:1724-1729 (1990).

Gines et al. "Effects of satavaptan, a selective vasopressin $V_2$ receptor antagonist, on ascites and serum sodium in cirrhosis with hyponatremia: A randomized trial" Hepatology 48:204-213 (2008).

Goldsmith "Current treatments and novel pharmacologic treatments for hyponatremia in congestive heart failure" Am. J. Cardiol. 95(suppl):14B-23B (2005).

Hassan et al. "Aryl-aryl bond formation one century after the discovery of the Ullmann reaction" Chem. Rev. 102:1359-1469 (2002).

Illarionov et al. "Sequence of the cDNA encoding the $Ca^2$-activated photoprotein obelin from the hydroid polyp Obelia longissima" Gene 153:273-274 (1995).

Kahn et al. "Management of cardiovascular disease in patients with kidney disease" Nat. Rev. Cardiol. 10:261-273 (2013).

Lemmens-Gruber et al. "Drugs of the future: Review vasopressin antagonists" Cell. Mol. Life Sci. 63:1766-1779 (2006).

Li et al. "Controlled and cardiac-restricted overexpression of the arginine vasopressin V1A receptor causes reversible left ventricular dysfunction through $G_{\alpha q}$-mediated cell signaling" Circulation 124:572-581 (2011).

Milligan et al. "$G_{16}$ as a universal G protein adapter: Implications for agonist screening strategies" Trends Pharmacol. Sci. 17:235-237 (1996).

Noble & Shurpik "The effect of pressure on some sterically hindered solvolysis reactions" J. Org. Chem. 35:3588-3589 (1970).

Omura & Swern "Oxidation of alcohols by 'activated' dimethyl sulfoxide. A preparative, steric and mechanistic study" Tetrahedron 34:1651-1660 (1978).

Palm et al. "Vasopressin antagonists as aquaretic agents for the treatment of hyponatremia" Am. J. Med. 119:587-592 (2006).

Papadopoulos "Friedel-crafts thioacylation with ethoxycarbonyl isothiocyanate. A one-step synthesis of aromatic thioamides" J. Org. Chem. 41:962-965 (1976).

Patani & Lavoie "Bioisosterism: a rational approach in drug design" Chem. Rev. 96:3147-3176 (1996).

Qiao & Lam "Copper-promoted carbon-heteroatom bond cross-coupling with boronic acids and derivatives" Synthesis 6:0829-0856 (2011).

Rao & Wu "Chan-Lam coupling reactions: Synthesis of heterocycles" Tetrahedron 68:7735-7754 (2012).

Rizzuto et al. "Rapid changes of mitochondrial $Ca^2$ revealed by specifically targeted recombinant aequorin" Nature 358:325-327 (1992).

Sanghi et al. "Vasopressin antagonism: A future treatment option in heart failure" Eur. Heart J. 26:538-543 (2005).

Santillan et al. "Vasopressin in preeclampsia a novel very early human pregnancy biomarker and clinically relevant mouse model" Hypertension 64:852-859 (2014).

Schrier et al. "Hormones and hemodynamics in heart failure" New Engl. J. Med. 341:577-585 (1999).

Schrier "The sea with us: Disorders of body water homeostasis" Curr. Opn. Invest. Drugs 8:304-311 (2007).

Tang et al. "Vasopressin receptor antagonists in the management of acute heart failure" Exp. Opn. Invest. Drugs 14:593-600 (2005).

Taveau et al. "Vasopressin and hydration play a major role in the development of glucose intolerance and hepatic steatosis in obese rats" Diabetologia 58:1081-1090 (2015).

Thibonnier & Roberts "Characterization of human platelet vasopressin receptors" J. Clin. Invest. 76:1857-1864 (1985).

Undeutsch & Halfbrodt "Citation of NMR peaklist data within patent applications" Research Disclosure database No. 605005 (Aug. 2014).

Verbalis "AVP receptor antagonists as aquaretics: Review and assessment of clinical data" Cleveland Clinic J. Med. 73:S24-S33 (2006).

Ward et al. "Synthesis of (−)-bactobolin from D-glucose and from (+)-actinobolin" Tetrahedron Lett. 35:3485-3488 (1994).

Wasilewski et al. "Arginine vasopressin receptor signaling and functional outcomes in heart failure" Cellular Signalling 28:224-233 (2016).

International Search Report for PCT/EP2017/060356, four pages, dated Jun. 20, 2017.

Written Opinion of the ISA for PCT/EP2017/060356, eight pages, dated Jun. 20, 2017.

AMIDE-SUBSTITUTED PYRIDINYLTRIAZOLE DERIVATIVES AND USES THEREOF

This application claims priority benefit of Application No. EP 16168165.5, filed May 3, 2016; the entire content of which is hereby incorporated by reference.

The present invention relates to novel 5-(carboxamide)-1-pyridinyl-1,2,4-triazole derivatives, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

Vasopressin is a neurohormone which basically regulates water homeostasis and vascular tone. It is produced in specialized endocrine neurons in the *Nucleus supraopticus* and *N. paraventricularis* in the wall of the third ventricle (hypothalamus) and is transported from there along the neural processes into the posterior lobes of the hypophysis (neurohypophysis). There, the hormone is released into the bloodstream in response to different physiological and pathophysiological stimuli. A disturbed neurohormonal regulation essentially manifests itself in an elevation of the sympathetic tone and inappropriate activation of the renin-angiotensin-aldosterone system (RAAS). While the inhibition of these components by beta-receptor blockers on the one hand and by ACE inhibitors or angiotensin-receptor blockers on the other is now an inherent part of the pharmacological treatment of cardiovascular diseases, the inappropriate elevation of vasopressin secretion is at present still not adequately treatable.

Vasopressin exerts its action mainly via binding to three receptors, which are classified as V1a, V1b and V2 receptors and which belong to the family of G protein-coupled receptors.

V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells. Consequently, pharmacological inhibition of the action of vasopressin on the V2 receptor results in increased urine excretion. Hence, drugs with V2 antagonistic activity appear particularly suitable for the treatment of all disease conditions which are associated with an overloading of the body with water.

V1b receptors (also named V3 receptors) are mainly detectable in the central nervous system. Together with corticotropin-releasing hormone (CRH), vasopressin regulates the basal and stress-induced secretion of adrenocorticotropic hormone (ACTH) via the V1b receptor.

V1a receptors are mainly located on vascular smooth muscle cells (VSMC) but also on cardiomyocytes, fibroblasts and specialized renal cells like glomerular mesangial cells or cells of the macula densa which control the release of renin [Wasilewski M A, Myers V D, Recchia F A, Feldman A M, Tilley D G, *Cell Signal.*, 28(3), 224-233, (2016)]. The activation of VSMC V1a receptor by vasopressin gives rise to intracellular calcium release and according vasoconstriction. Therefore, stimulation of VSMC V1a receptors causes increased vascular resistance and increased cardiac afterload. Cardiac output is adversely affected by V1a-mediated vasoconstriction. The increase in afterload and direct stimulation of V1a receptors on cardiomyocytes can lead to cardiac hypertrophy and remodeling including fibrosis. Mice with cardiac-specific overexpression of V1a receptor develop cardiac hypertrophy leading to dilation and left ventricular dysfunction, suggesting an essential role for V1a receptor in the development of heart failure [Li X, Chan T O, Myers V, Chowdhury I, Zhang X Q, Song J, Zhang J, Andrei J, Funakoshi H, Robbins J, Koch W J, Hyslop T, Cheung J Y, Feldman A M, *Circulation.*; 124, 572-581 (2011)].

V1a receptor is also expressed in the renal cortical and medullary vasculature, where it mediates vasoconstriction of renal vessels and affecting overall renal blood flow. Thus, the activation of V1a receptor can decrease renal medullary blood flow inducing further pathological processes as tissue hypoxia, reduced oxygen and accordingly energy supply for tubular transport processes as well as direct damages of mesangial and macula densa cells. It has been demonstrated that mesangial V1a receptor activation mediates TGFβ signaling and causes an increase in production of collagen IV. While this signaling contributes to extracellular matrix accumulation and remodeling in the kidney, similar signaling pathways are believed to occur in cardiac cells especially after myocardial infarction, which emphasizes the central role of V1a receptor in the development of hypertrophic and fibrotic processes in response to pathophysiological elevated vasopressin levels [Wasilewski M A, Myers V D, Recchia F A, Feldman A M, Tilley D G. *Arginine vasopressin receptor signaling and functional outcomes in heart failure. Cell Signal.*, 28(3), 224-233 (2016)].

Since V1a receptors are mainly expressed on VSMCs and thus participating in vascular function, a link to vascular diseases as peripheral arterial disease (PAD) including claudication and critical limb ischemia as well as coronary microvascular dysfunction (CMD) is conceivable.

Apart from this, V1a receptors are also expressed on human platelets and in the liver. The meaning of platelet V1a receptors is not fully understood although vasopressin induces aggregation of human platelets via V1a receptor at high concentrations ex vivo. Therefore, inhibition of vasopressin-induced platelet aggregation by V1a receptor antagonists is a useful pharmacological ex vivo assay making use of human tissue endogenously expressing the V1a receptor [Thibonnier M, Roberts J M, *J Clin Invest.*; 76:1857-1864, (1985)].

Vasopressin stimulates gluconeogenesis and glycogenolysis via activation of the hepatic V1a receptor. Animal studies have shown that vasopressin impairs glucose tolerance which could be inhibited by a V1a receptor antagonist thereby providing a link of vasopressin receptor V1a to diabetes mellitus. [Taveau C, Chollet C, Waeckel L, Desposito D, Bichet D G, Arthus M F, Magnan C, Philippe E, Paradis V, Foufelle F, Hainault I, Enhorning S, Velho G, Roussel R, Bankir L, Melander O, Bouby N. Vasopressin and hydration play a major role in the development of glucose intolerance and hepatic steatosis in obese rats. Diabetologia, 58(5), 1081-1090, (2015)]. Vasopressin was shown to contribute to the development of albuminuria and to diabetes-induced nephropathy in animal models which is consistent with epidemiological findings in humans.

It was found recently that vasopressin also seems to play a causal role in the development of preeclampsia. Chronic infusion of vasopressin during pregnancy in mice is sufficient to induce all of the major maternal and fetal phenotypes associated with human preeclampsia, including pregnancy-specific hypertension [Santillan M K, Santillan D A, Scroggins S M, MIN J Y, Sandgren J A, Pearson N A, Leslie K K, Hunter S K, Zamba G K, Gibson-Corley K N, Grobe J L. Vasopressin in preeclampsia: a novel very early human pregnancy biomarker and clinically relevant mouse model. Hypertension. 64(4), 852-859, (2014)].

Vasopressin levels can be elevated in women with dysmenorrhoea (a gynecological disorder which is characterised by cyclical cramping pelvic pain) during menstruation, which appear to increase myometrial smooth muscle contraction. It was found recently that a selective vasopressin V1a receptor antagonist (relcovaptan/SR-49059) can reduce intrauterine contractions elicited by vasopressin.

For these reasons, agents which inhibit the action of vasopressin on the V1a receptor appear suitable for the treatment of several cardiovascular diseases. In particular, agents which inhibit the action of vasopressin selectively on the V1a receptor offer an especially ideal profile for the treatment of otherwise normovolemic patients, i.e. those which are not eligible for decongestion by e.g. high doses of loop diuretics or V2 antagonists, and where induced aquaresis via V2 inhibition may be undesired.

Certain 4-phenyl-1,2,4-triazol-3-yl derivatives have been described in WO 2005/063754-A1 and WO 2005/105779-A1 to act as vasopressin V1a receptor antagonists that are useful for the treatment of gynecological disorders, notably menstrual disorders such as dysmenorrhea.

In WO 2011/104322-A1, a particular group of bis-aryl-bonded 1,2,4-triazol-3-ones, including 5 phenyl-1,2,4-triazol-3-yl and 1-phenyl-1,2,3-triazol-4-yl derivatives thereof, has been disclosed as antagonists of vasopressin V2 and/or V1a receptors being useful for the treatment and/or prevention of cardiovascular diseases. The described compounds, however, do not show sufficient selectivity towards the V1a receptor and mostly show combined activity on both vasopressin V1a and V2 receptors. Yet, as outlined above, a high affinity as well as selectivity for the V1a receptor is a desirable prerequisite for the treatment of disease conditions where a decongestion is not desired and may lead to a dysregulated body fluid homeostasis including decreased blood plasma osmolality in otherwise normovolemic individuals.

In WO 2016/071212-A1 certain 5-(hydroxyalkyl)-1-phenyl-1,2,4-triazole derivatives have been disclosed, which act as potent antagonists of both vasopressin V1a and V2 receptors and, in addition, exhibit significantly enhanced aquaretic potency in vivo after oral application. The compounds are described to be useful for the treatment and/or prevention of cardiovascular and renal diseases. Yet, as outlined above, a high affinity as well as selectivity for the V1a receptor is a desirable prerequisite for the treatment of disease conditions where a decongestion is not desired and may lead to a dysregulated body fluid homeostasis including decreased blood plasma osmolality in otherwise normovolemic individuals.

An activity profile with a high selectivity for the V1a receptor has a low potential to cause unwanted off-target related side effects and would also help towards reducing the amount of substance which is going to be required to achieve and maintain the desired therapeutic effect, thus limiting the potential for unacceptable side effects and/or unwanted drug-drug interactions during the treatment of patients which might already be at high risk, such as, for example, in acute or chronic heart and kidney diseases.

The technical problem to be solved according to the present invention may therefore be seen in identifying and providing new compounds that act as potent antagonists of the vasopressin V1a receptor. A further object of the invention is to identify and provide new compounds with a high affinity and selectivity vis-à-vis the vasopressin V1a receptor. The compounds are intended to avoid inducing aquaresis via V2 inhibition. The compounds are further intended to have a similar or improved therapeutic profile compared to the compounds known from the prior art, for example with respect to their in vivo properties, for example their pharmacokinetic and pharmacodynamic characteristics and/or their metabolic profile and/or their dose-activity relationship.

Surprisingly, it has now been found that certain 5-(carboxamide)-1-pyridinyl-1,2,4-triazole derivatives represent highly potent and selective antagonists of the V1a receptor. This specific profile renders the compounds of the present invention useful for the treatment and/or prevention of diseases, which are associated with V1a receptor activation. The compounds of the present invention are particularly useful for the treatment and/or prevention of renal and cardiovascular diseases in subjects which do not suffer from fluid overload and who therefore should not be decongested.

The compounds of the present invention have valuable pharmacological properties and can be used for the prevention and/or treatment of various diseases and disease-induced states in humans and other mammals.

In one aspect, the present invention relates to 5-(carboxamide)-1-pyridinyl-1,2,4-triazole derivatives of the general formula (I)

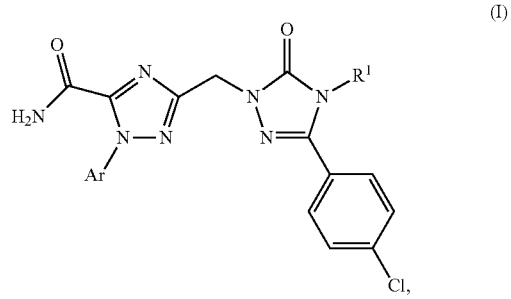

in which
$R^1$ represents a group of the formula

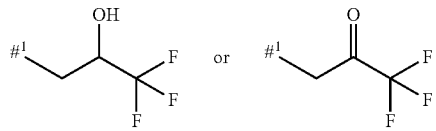

in which
$\#^1$ represents the point of attachment to the nitrogen atom,
Ar represents a group of the formula

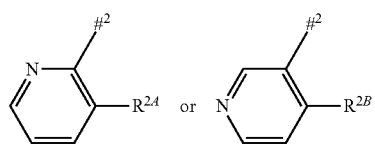

in which
$\#^2$ represents the point of attachment to the nitrogen atom,
$R^{2A}$ represents a group selected from a chlorine atom, a bromine atom, trifluoromethyl, trifluoromethoxy, ethoxycarbonyl and —C(=O)NH$_2$,
$R^{2B}$ represents a group selected from a chlorine atom, trifluoromethyl, and ethoxycarbonyl.

The compounds according to this invention can also be present in the form of their salts, solvates and/or solvates of the salts.

The term "comprising" when used in the specification includes "consisting of".

If within the present text any item is referred to as "as mentioned herein", it means that it may be mentioned anywhere in the present text.

The terms as mentioned in the present text have the following meanings:

The term "$C_1$-$C_4$-alkyl" means a linear or branched, saturated, monovalent hydrocarbon group having 1, 2, 3, or 4 carbon atoms, e.g. a methyl, ethyl, propyl, isopropyl, butyl, sec-butyl, isobutyl, tert-butyl, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group, even more particularly a methyl group.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a direct route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention optionally contain one asymmetric centre, depending upon the location and nature of the various substituents desired. It is possible that one asymmetric carbon atom is present in the (R) or (S) configuration, which can result in racemic mixtures. In certain instances, it is possible that asymmetry also be present due to restricted rotation about a given bond, for example, the central bond adjoining two substituted aromatic rings of the specified compounds. Preferred compounds are those which produce the more desirable biological activity. Separated, pure or partially purified isomers and stereoisomers or racemic mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials. In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates. Hydrates are preferred solvates in the context of the present invention.

In particular, the 3,3,3-trifluoro-2-oxopropyl derivatives of the formula (I-B) according to the invention (ketone form) may also be present in the 3,3,3-trifluoro-2,2-dihydroxypropyl form (I-B)' (hydrate form) (see Scheme 1 below); both forms are expressly embraced by the present invention.

Scheme 1

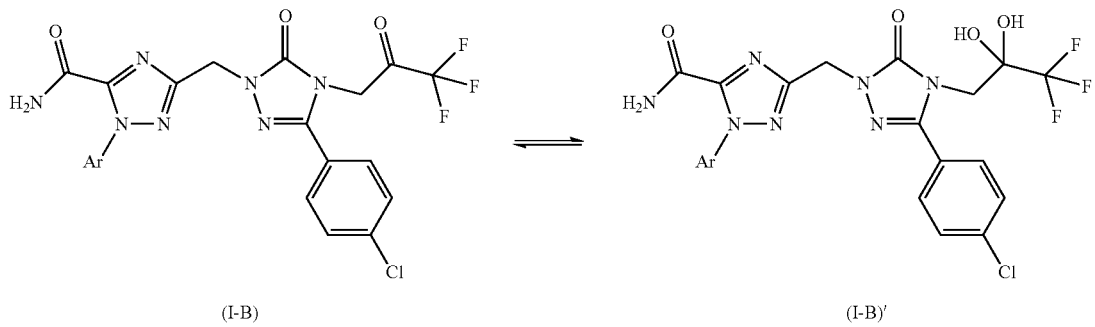

(I-B)          (I-B)'

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

In a distinct embodiment, the present invention relates to compounds of formula (I), supra, wherein
R$^1$ represents a group of the formula

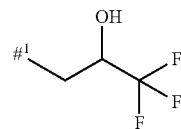

in which
$^1$ represents the point of attachment to the nitrogen atom,
Ar represents a group of the formula

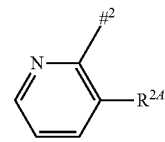

in which
$^2$ represents the point of attachment to the nitrogen atom,
R$^{2A}$ represents a group selected from a chlorine atom, a bromine atom, trifluoromethyl, trifluoromethoxy, ethoxycarbonyl and —C(=O)NH$_2$,
or a pharmaceutically acceptable salt, hydrate and/or solvate thereof.

In a preferred embodiment, the present invention relates to compounds according to formula (I), supra, wherein
R$^1$ represents a group of the formula

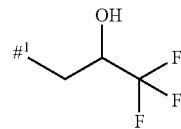

in which
$^1$ represents the point of attachment to the nitrogen atom,
Ar represents a group of the formula

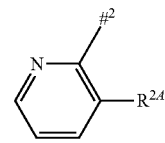

in which
² represents the point of attachment to the nitrogen atom,
R²·ᴬ represents a group selected from a chlorine atom, trifluoromethyl and trifluoromethoxy,
or a pharmaceutically acceptable salt, hydrate and/or solvate thereof.

In accordance with a further preferred embodiment, the present invention covers compounds of general formula (I), supra, wherein
R¹ represents a (2S)-3,3,3-trifluoro-2-hydroxypropyl group of the formula

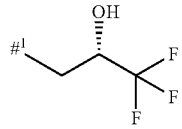

in which
¹ represents the point of attachment to the nitrogen atom,
or a pharmaceutically acceptable salt, hydrate and/or solvate thereof.

R¹ represents a (2R)-3,3,3-trifluoro-2-hydroxypropyl group of the formula

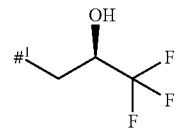

in which
¹ represents the point of attachment to the nitrogen atom,
or a pharmaceutically acceptable salt, hydrate and/or solvate thereof.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (II), (III), (IV), (V), (VI) and (VIII), (VIII). The present invention covers the compounds of general formula (I) which are disclosed in the Example Section of this text, infra.

In accordance with a second aspect, the present invention covers methods of preparing compounds of general formula (I) as defined supra, said methods comprising the step
[A] of allowing an intermediate compound of formula (II):

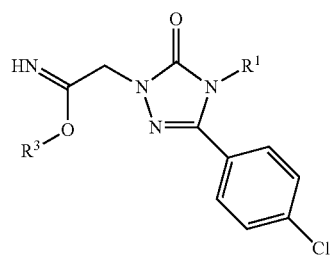

in which R' is as defined for the compound of general formula (I) as defined supra, and
R³ represents a (C₁-C₄)-alkyl group, in particular a methyl group,
to react in a first step in the presence of a base with a compound of general formula (III):

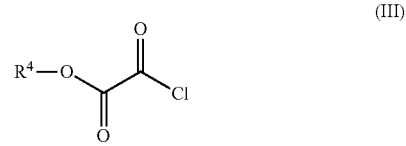

in which
R⁴ represents a (C₁-C₄)-alkyl group, in particular a methyl group,
to give an intermediate compound, which is then allowed to react in the presence of a base, and optionally a copper salt, in a second step with a hydrazine compound of general formula (IV) or a respective salt thereof

in which Ar is as defined for the compound of general formula (I) as defined supra, thereby giving a compound of general formula (V):

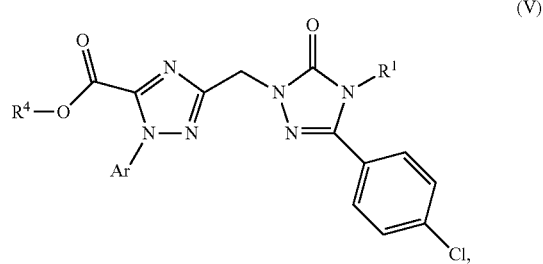

in which R¹ and Ar are as defined for the compound of general formula (I) as defined supra, and
R⁴ represents a (C₁-C₄)-alkyl group, in particular a methyl group, followed by a subsequent step
[B] of allowing the compound of formula (V) obtained in step [A] to react with ammonia thereby giving a compound of general formula (I):

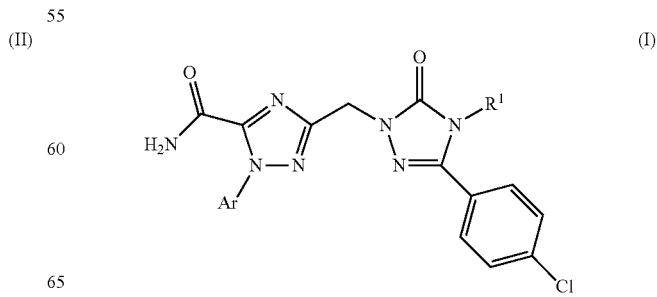

in which R[1] and Ar are as defined for the compound of general formula (I) as defined supra, optionally followed by step

[C] conversion of the alcohols of general formula (I-A):

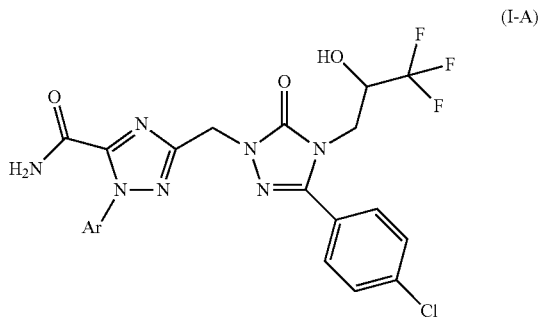

(I-A)

in which Ar is as defined for the compound of general formula (I) as defined supra, to the ketones of general formula (I-B):

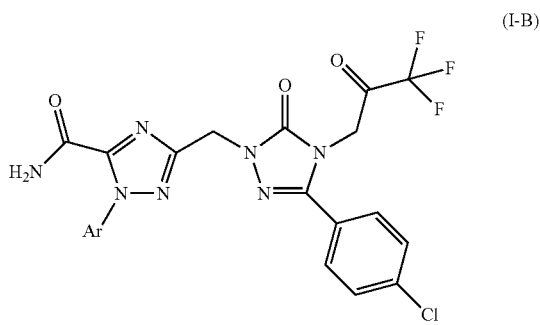

(I-B)

in which Ar is as defined for the compound of general formula (I) as defined supra, using known oxidation methods, each [A], [B] and [C] optionally followed, where appropriate, by (i) separating the compounds of formula (I) thus obtained into their respective enantiomers, and/or (ii) converting the compounds of formula (I) into their respective hydrates, solvates, salts and/or hydrates or solvates of the salts by treatment with the corresponding solvents and/or acids or bases.

The present invention covers methods of preparing compounds of the present invention of general formula (I), said methods comprising the steps as described in the Experimental Section herein.

The schemes and procedures described below illustrate synthetic routes to the compounds of general formula (I) of the invention and are not intended to be limiting. It is clear to the person skilled in the art that the order of transformations as exemplified in schemes 2, 3, 4, 5, 6 and 7 can be modified in various ways. The order of transformations exemplified in these schemes is therefore not intended to be limiting. In addition, interconversion of any of the substituents, R[1], R[2], R[3], R[4] and Ar can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis,* 3rd edition, Wiley 1999). Specific examples are described in the subsequent paragraphs.

The multicomponent cyclization (II)→(V) is carried out by first reacting imidate of formula (II) with an acid chloride of formula (III) in the presence of a base to form an intermediate which is in a subsequent step reacted with the aryl hydrazine compound of formula (IV). Typically the formed intermediate is not isolated and the reaction over the two steps is performed in one-pot. The arylhydrazine compound for formula (I) may also be used in form of its salts, such as a hydrochloride salt or a tosylate salt. Under the alkaline reaction conditions, the hydrazine salt will be reconverted into the free base form. The amount of base added may then be adjusted in this respect. It may be beneficial in the second step to add a copper or zinc salt, such as copper(II) sulfate, copper(II) chloride, zinc(II) sulfate and zinc(II) chloride typically and preferably copper(II) sulfate and zinc(II) sulfate are used.

Suitable bases for both steps are typically tertiary amine bases, such as N,N-diisopropylethylamine (DIPEA), triethylamine, triisopropylamine, N-methylimidazole, N-methylmorpholine, pyridine and 4-(N,N-dimethylamino)pyridine. Preferably, N,N-diisopropylethylamine (DIPEA) is used as base. The reaction is performed in an inert organic solvent, such as dichloromethane, 1,2-dichloroethane, methyl tert-butyl ether, tetrahydrofuran, 1,4-dioxane, 1,2-dimethoxyethane, toluene, pyridine, ethyl acetate, acetonitrile or N,N-dimethylformamide, or in a mixture of these solvents. Preferably tetrahydrofuran or dioxane or a mixture thereof are used as solvents. The first step is generally carried out at a temperature in the range of −10° C. to +120° C., preferably at 0° C. The second step is generally carried out at a temperature in the range of +20° C. to +120° C., preferably at room temperature. Concomitant microwave irradiation may have a beneficial effect in this reaction as well at a temperature in the range of +60° C. to +150° C., preferably at +120° C.

The aminolysis reaction (V)→(I) is usually carried out in a solution of ammonia. Suitable ammonia solutions for this step are saturated ammonia solutions, in particular a solution of ammonia in methanol, ethanol, isopropanol, tetrahydrofuran, dioxane or water or a mixture thereof. Preferably, a methanolic ammonia solution is used. The reaction is preferably performed directly in the ammonia solution in the absence of any further reaction solvent. This step is generally carried out at a temperature in the range of +20° C. to +120° C., preferably at room temperature. Concomitant microwave irradiation may have a beneficial effect in this reaction as well at a temperature in the range of +60° C. to +150° C., preferably at +120° C.

The oxidation reaction (I-A)→(I-B) is carried out using customary oxidation methods known from the literature [e.g. JOC, 1983, 48, 4155 (Dess Martin oxidation); Tet Lett, 1994, 35, 3485 (IBX oxidation); JOC, 1970, 35, 3589 (acid dichromate oxidation); Tet Lett, 1979, 399 (PDC oxidation); Tetrahedron, 1978, 34, 1651 (Swern oxidation)]. Thus, the alcohol group in the compounds of the general formula (I-A) is preferably oxidized using Dess-Martin periodinane (DMP). In a typical procedure the reaction is carried out in dichloromethane at a temperature of 0° C. and subsequent warming up to room temperature.

Compounds of general formula (II) as defined supra, can be prepared by a method comprising the step

[a] of allowing an intermediate compound of formula (VI):

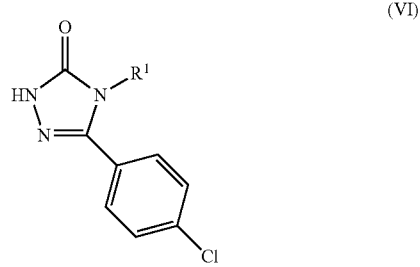

(VI)

in which R¹ is as defined for the compound of general formula (I) as defined supra, to react with a nitrile compound of general formula (VII),

(VII)

in which X represents a leaving group, such as chlorine, bromine, iodine, mesylate or tosylate, in particular chlorine or bromine,
thereby giving a compound of general formula (VIII)

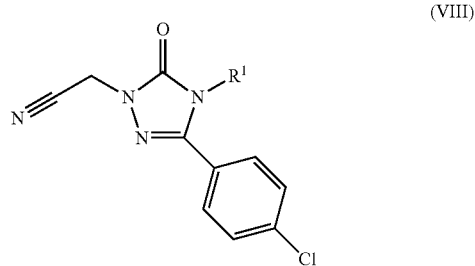

(VIII)

in which R¹ is as defined for the compound of general formula (I) as defined supra, followed by a subsequent step

[b] of allowing the compound of formula (VIII) obtained in step [a] to react with a basic alcoholate, preferably sodium methanolate, thereby giving a compound of general formula (II),

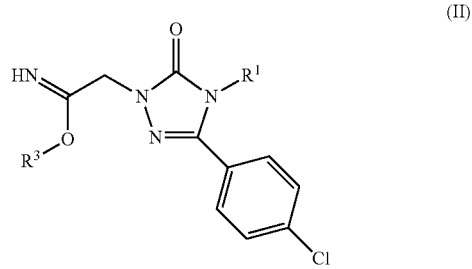

(II)

in which R¹ is as defined for the compound of general formula (I) as defined supra, and R³ represents a $(C_1-C_4)$-alkyl group, in particular a methyl group.

The N-alkylation reaction (VI)+(VII)→(VIII) (step [a]) is typically carried out in the presence of a base. Typical and exemplary bases include sodium carbonate, potassium carbonate, cesium carbonate, N,N-diisopropylethylamine, triethylamine, sodium tert-butylate or potassium tert-butylate in acetonitrile, methylisobutylketone, dioxane, dimethylformamide, dimethylacetamide, N-methylpyrrolidinone, dimethylsulfoxide and sulfolane, preference is given to potassium carbonate in methylisobutylketone or acetonitrile. The reaction may optionally be carried out in an advantageous manner with addition of an alkylation catalyst such as, for example, lithium bromide, sodium iodide, lithium iodide, tetra-n-butylammoniumbromide, tetra-n-butylammoniumiodide or benzyltriethylammoniumchloride. The reactions are generally carried out in a temperature range of from +40° C. to +120° C., preferably at from +60° C. to +80° C. The reactions can be carried out at atmospheric, at elevated or at reduced pressure (for example at from 0.5 to 5 bar); in general, the reactions are carried out at atmospheric pressure. It may be advantageous to slowly perform the addition of the alkylation agent (VII) over a longer time span.

Conversion to the imidate of general formula (II) can be achieved via standard reaction protocols known to the person skilled in the art (step [b]: (VIII)→(II)). The reaction is typically carried out under basic reactions conditions by reacting with a basic alcoholate. Typical bases, which may be used are sodium methanolate, sodium ethanolate, sodium propanolate, sodium isopropoxide, sodium tert-butylate or potassium tert-butylate in methanol, ethanol, n-propanol, isopropanol, n-butanol, isobutanol and tert-butanol. Preference is given to sodium methanolate in methanol. The reactions are generally carried out in a temperature range of from +20 to +80° C., preferably at from +20 to +40° C.

Alternatively, the nitrile compounds of general formula (VIII) may optionally also be prepared as shown in the synthetic scheme 2 below:

Scheme 2

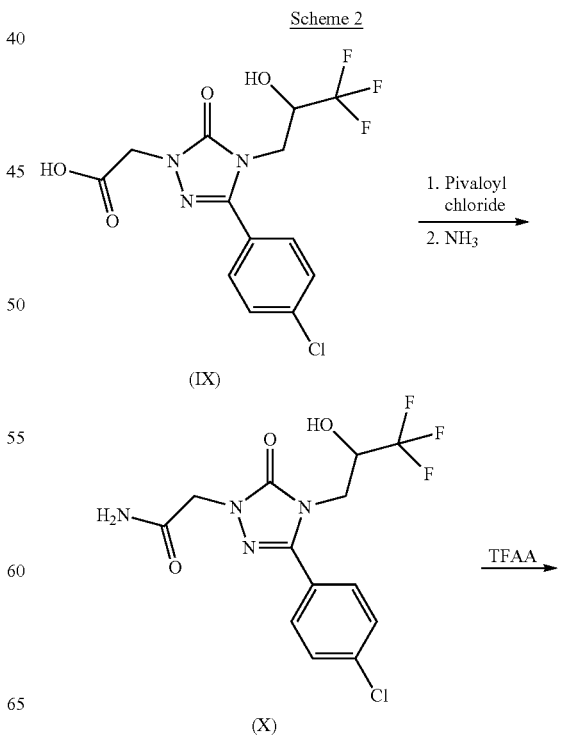

-continued

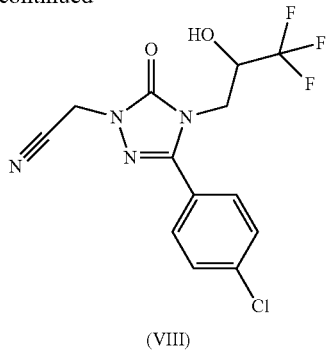

(VIII)

TFAA=trifluoroacetic acid anhydride

The amide coupling (IX)→(X) can be carried out directly with the help of a condensing agent or activating agent in the presence of a base or over two steps via an acyl chloride or carboxylic acid imidazolide. Typical condensation and activating agents for the amide formation in process steps (IX)→(X) include, for example, carbodiimides such as N,N'-diethyl-, N,N'-dipropyl-, N,N'-diisopropyl-N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3-sulphate or 2-tert-butyl-5-methyl-isoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazo-lidinyl)phosphoryl chloride, benzotriazol-1-yloxytris(dimethylamino)phosphonium hexafluorophosphate, benzotriazol-1-yloxytris(pyrrolidino) phosphonium hexafluorophosphate (PyBOP), O-(benzotriazol-1-yl)-N, N, N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluroniumhexafluorophosphate (HATU) or O-(1H-6-chlorobenzotriazol-1-yl)-1,1,3,3-tetramethyluronium tetrafluoroborate (TCTU), optionally in combination with other additives such as 1-hydroxybenzotriazole (HOBt) or N-hydroxysuccinimide (HOSu). The acyl chlorides are typically prepared with thionyl chloride or oxalyl chloride in an inert solvent like dichloromethane or N,N-dimethylformamide. It is also possible to use mixtures of the solvents mentioned Typical and exemplary bases include sodium carbonate, potassium carbonate, cesium carbonate, N,N-diisopropylethylamine, triethylamine, sodium tert-butylate or potassium tert-butylate in acetonitrile, methylisobutylketone, dioxane, dimethylformamide, dimethylacetamide, N-methylpyrrolidinone, dimethylsulfoxide and sulfolane, preference is given to potassium carbonate in methylisobutylketone or acetonitrile. The reaction may optionally be carried out in an advantageous manner with addition of an alkylation catalyst such as, for example, lithium bromide, sodium iodide, lithium iodide, tetra-n-butylammoniumbromide, tetra-n-butylammoniumiodide or benzyltriethylammoniumchloride. The conversion to the nitrile (X)→(XI) can be carried out with the help of dehydrating agent. Typical dehydrating agents include, for example trifluoroacetic acid anhydride, phosphorous pentoxide (P$_4$O$_{10}$), phosphoryl chloride (POCl$_3$), phosphorous pentachloride (PCl$_5$), CCl$_4$—PPh$_3$ (Appel reagent), hexamethylphosphoramide (HMPA); methyl N-(triethyl-ammoniumsulfonyl)carbamate (Burgess reagent), (Chloromethylene)dimethyliminium chloride (Vilsmeier reagent), oxalyl chloride/DMSO and thionylchloride (SOCl$_2$).

Typical and exemplary solvents for both steps (IX)→(X) and (X)→(XI) include for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil, fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N'-dimethylpropyleneurea (DMPU) or N-methylpyrrolidone (NMP). It is also possible to use mixtures of the solvents mentioned.

In a typical and preferred procedure the carboxylic acid (IX) is first reacted with pivaloyl chloride in the presence of pyridine to form an intermediate which is in a subsequent step reacted with ammonia. Typically the formed intermediate is not isolated and the reaction over the two steps is performed in one-pot. Suitable as bases for the first step are preferably, pyridine, 4-(N,N-dimethylamino)pyridine or N,N-diisopropylethylamine (DIPEA). The conversion of carboxamide (X) into nitrile (VIII) is then typically performed by reaction with trifluoroacetic anhydride. Both reactions are conducted in an inert organic solvent, preferably tetrahydrofuran.

The compounds of formula (VI) and (IX) can be synthesized by the procedures described in Int. Pat. Appl. WO 2010/105770 and WO 2011/104322 (see also synthesis schemes 3 and 4 below).

The compounds of the formulae (III), (IV) and (VII) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The preparation of the compounds of the invention may be illustrated by means of the following synthesis schemes:

Scheme 3

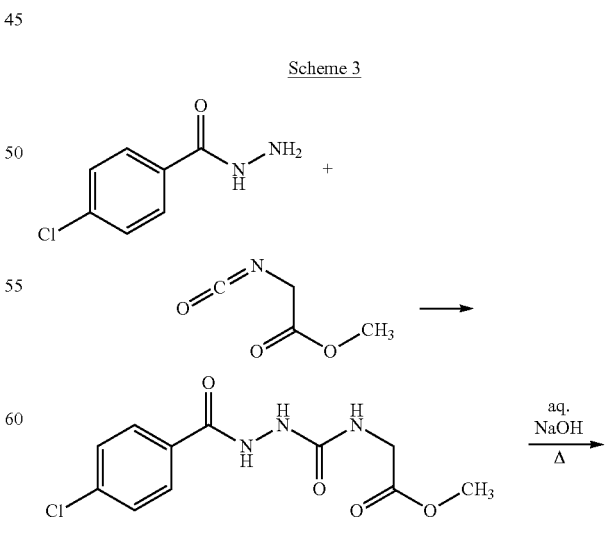

19
-continued
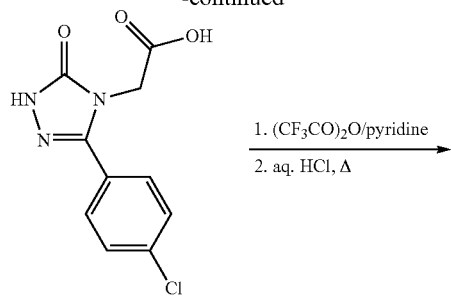
1. (CF₃CO)₂O/pyridine
2. aq. HCl, Δ
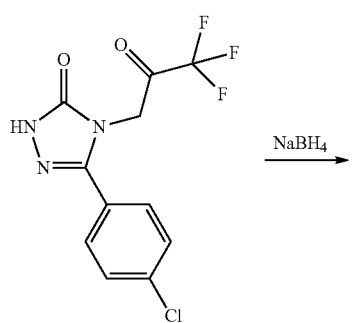
NaBH₄ →
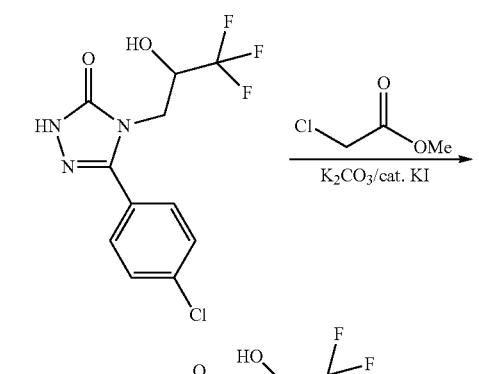
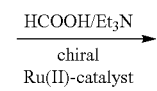 ClCH₂C(O)OMe / K₂CO₃/cat. KI →
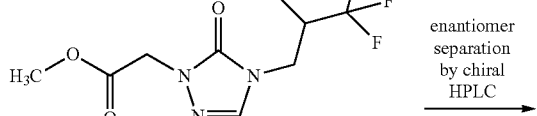
enantiomer separation by chiral HPLC →
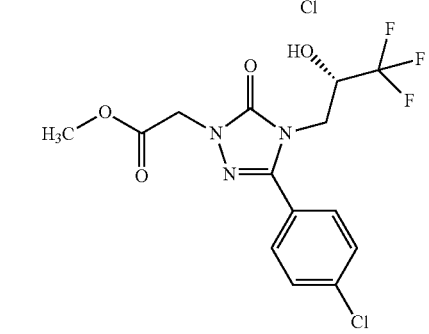
+
20
-continued
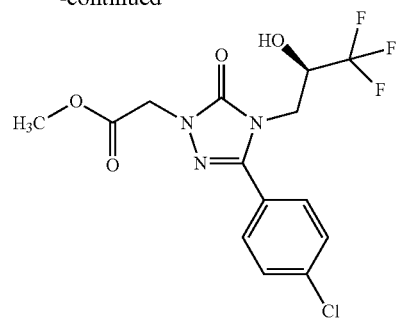
[cf. Int. Pat. Appl. WO 2011/104322-A1].
Scheme 4
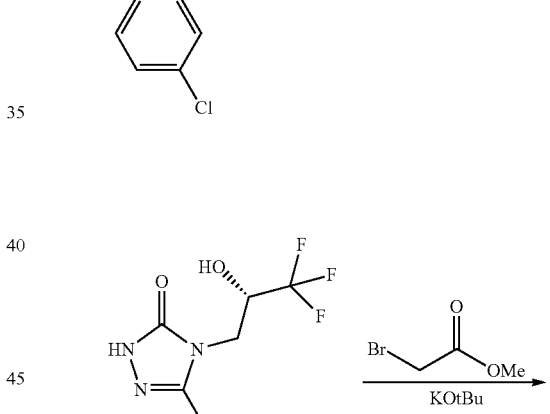
HCOOH/Et₃N chiral Ru(II)-catalyst →
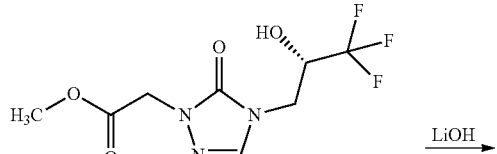
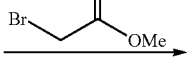 BrCH₂C(O)OMe / KOtBu →
 LiOH →

[cf. Int. Pat. Appl. WO 2011/104322-A1].

Scheme 5

Scheme 6

Scheme 7

TFAA: trifluoroacetic acid anhydride

-continued

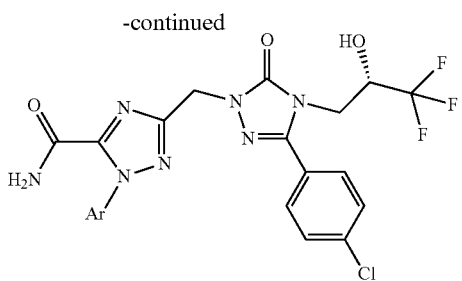

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

The compounds of the present invention have valuable pharmacological properties and can be used for the prevention and/or treatment of various diseases and disease-induced states in humans and other mammals. Compounds of general formula (I) of the present invention demonstrate a valuable pharmacological spectrum of action and pharmacokinetic profile, both of which could not have been predicted. Compounds of the present invention have surprisingly been found to effectively inhibit the vasopressin V1a receptor and it is possible therefore that said compounds be used for the treatment and/or prevention of diseases, preferably renal and cardiovascular diseases in humans and animals.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of formula (I)" is meant to include the simultaneous treatment of more than one disease as well as the administration of more than one compound of formula (I).

The compounds of the present invention are highly potent and in particular selective antagonists of the vasopressin V1a receptor. The compounds of the invention are therefore expected to be highly valuable as therapeutic agents for the treatment and/or prevention of diseases, in particular for the treatment and/or prevention of renal and cardiovascular diseases.

As used herein, the term "vasopressin V1a receptor antagonist" refers to a compound that functions by inhibiting (partially or completely) or blocking the vasopressin V1a receptor, thereby preventing activation of the receptor by vasopressin.

In one embodiment, compounds described herein are active at the V1a receptor. In another embodiment compounds described herein exhibit inhibition of the V1a receptor according to the study in B-1 with an $IC_{50}<100$ nM. In another embodiment compounds described herein exhibit inhibition of the V1a receptor according to the study in B-1 with an $IC_{50}<20$ nM. In another embodiment compounds described herein exhibit inhibition of the V1a receptor according to the study in B-1 with an $IC_{50}<10$ nM. In another embodiment compounds described herein exhibit inhibition of the V1a receptor according to the study in B-1 with an $IC_{50<5}$ nM. In another embodiment compounds described herein exhibit inhibition of the V1a receptor according to the study in B-1 with an $IC_{50}<2$ nM.

In a further embodiment, compounds described herein are selectively active at the V1a receptor, and are less active, substantially less active, and/or inactive at other vasopressin receptors, such as the V1b and/or V2 subtypes. In another embodiment, compounds described herein are at least 10-fold selective for the V1a receptor compared to the V2 receptor as determined according to the study in B-1. In another embodiment, compounds described herein are at least 15-fold selective for the V1a receptor compared to the V2 receptor as determined according to the study in B-1. In another embodiment, compounds described herein are at least 20-fold selective for the V1a receptor compared to the V2 receptor as determined according to the study in B-1. In another embodiment, compounds described herein are at least 30-fold selective for the V1a receptor compared to the V2 receptor as determined according to the study in B-1.

The compounds according to the invention are suitable for the treatment and/or prevention of renal diseases, in particular of acute and chronic kidney diseases, diabetic kidney diseases, and of acute and chronic renal failure. The general terms 'renal disease' or 'kidney disease' describe a class of conditions in which the kidneys fail to filter and remove waste products from the blood. There are two major forms of kidney disease: acute kidney disease (acute kidney injury, AKI) and chronic kidney disease (CKD). The compounds according to the invention may further be used for the treatment and/or prevention of sequelae of acute kidney injury arising from multiple insults such as ischemia-reperfusion injury, radiocontrast administration, cardiopulmonary bypass surgery, shock and sepsis. In the sense of the present invention, the term renal failure or renal insufficiency comprises both acute and chronic manifestations of renal insufficiency, as well as underlying or related kidney diseases such as renal hypoperfusion, intradialytic hypotension, obstructive uropathy, glomerulopathies, IgA nephropathy, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schnlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism. The compounds according to the invention are also suitable for the treatment and/or prevention of polycystic kidney disease (PCKD) and of the syndrome of inadequate ADH secretion (SIADH).

Cardiovascular diseases in this context that may be treated and/or prevented with the compounds of the invention include, but are not limited to, the following: acute and chronic heart failure including worsening chronic heart failure (or hospitalization for heart failure) and including congestive heart failure, arterial hypertension, resistant hypertension, arterial pulmonary hypertension, coronary heart disease, stable and unstable angina pectoris, atrial and ventricular arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node reentry tachycardia and Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction), furthermore thromboembolic diseases and ischaemias such as peripheral perfusion disturbances, reperfusion injury, arterial and venous thromboses, myocardial insufficiency, endothelial dysfunction, micro- and macrovascular damage (vasculitis) and for preventing restenoses such as after thrombolysis therapies, percutaneous transluminal angioplasty (PTA), percutaneous transluminal coronary angioplasty (PTCA), heart transplantation and bypass operations, arteriosclerosis, disturbances of lipid metabolism, hypolipoproteinaemias, dyslipidemias, hypertriglyceridemias, hyperlipidemias and combined hyperlipidemias, hypercholesterolaemias, abetalipoproteinaemia, sitosterolemia, xanthomatosis, Tangier disease, adipositas, obesity, metabolic syndrome, transitory and ischemic attacks, stroke, inflammatory cardiovascular diseases, peripheral and cardiac vascular diseases, peripheral circulation disorders, spasms of the coronary arteries and peripheral arteries, and edema such as, for example, pulmonary edema, cerebral edema, renal edema and heart failure-related edema.

In the sense of the present invention, the term heart failure also includes more specific or related disease forms such as right heart failure, left heart failure, global insufficiency, ischemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcoholtoxic cardiomyopathy, cardiac storage diseases, heart failure with preserved ejection fraction (HFpEF or diastolic heart failure), and heart failure with reduced ejection fraction (HFrEF or systolic heart failure).

The compounds of the present invention may be particularly useful for the treatment and/or prevention of the cardiorenal syndrome (CRS) and its various subtypes. This term embraces certain disorders of the heart and kidneys whereby acute or chronic dysfunction in one organ may induce acute or chronic dysfunction of the other.

Moreover, the compounds according to the invention may be used for the treatment and/or prevention of peripheral arterial disease (PAD) including claudication and including critical limb ischemia, coronary microvascular dysfunction (CMD) including CMD type 1-4, primary and secondary Raynaud's phenomenon, microcirculation disturbances, peripheral and autonomic neuropathies, diabetic microangiopathies, diabetic retinopathy, diabetic limb ulcers, gangrene, CREST syndrome, erythematous disorders, rheumatic diseases and for promoting wound healing.

Furthermore, the compounds of the invention are suitable for treating urological diseases and diseases of the male and female urogenital system such as, for example, benign prostatic syndrome (BPS), benign prostatic hyperplasia (BPH), benign prostatic enlargement (BPE), bladder outlet obstruction (BOO), lower urinary tract syndromes (LUTS), neurogenic overactive bladder (OAB), interstitial cystitis (IC), urinary incontinence (UI) such as for example mixed, urge, stress and overflow incontinence (MUI, UUI, SUI, OUI), pelvic pains, erectile dysfunction, dysmenorrhea and endometriosis.

The compounds according to the invention may also be used for the treatment and/or prevention of inflammatory diseases, asthmatic diseases, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF). In addition, the compounds of the invention may be used for the treatment and/or prevention of pulmonary arterial hypertension (PAH) and other forms of pulmonary hypertension (PH) including pulmonary hypertension associated with left ventricular disease, HIV infection, sickle cell anaemia, thromboembolism (CTEPH), sarcoidosis, chronic obstructive pulmonary disease (COPD) or pulmonary fibrosis.

Additionally, the compounds according to the invention may be used for the treatment and/or prevention of liver cirrhosis, ascites, diabetes mellitus and diabetic complications such as, for example, neuropathy and nephropathy.

Further, the compounds of the invention are suitable for the treatment and/or prevention of central nervous disorders such as anxiety states, depression, glaucoma, cancer such as in particular pulmonary tumors, and circadian rhythm misalignment such as jet lag and shift work.

Furthermore, the compounds according to the invention may be useful for the treatment and/or prevention of pain conditions, diseases of the adrenals such as, for example, pheochromocytoma and adrenal apoplexy, diseases of the intestine such as, for example, Crohn's disease and diarrhea, menstrual disorders such as, for example, dysmenorrhea, endometriosis, preterm labor and tocolysis.

Due to their activity and selectivity profile, the compounds of the present invention are believed to be particularly suitable for the treatment and/or prevention of acute and chronic kidney diseases including diabetic nephropathy, acute and chronic heart failure, preeclampsia, peripheral arterial disease (PAD), coronary microvascular dysfunction (CMD), Raynaud's syndrome and dysmenorrhea.

The diseases mentioned above have been well characterized in humans, but also exist with a comparable etiology in other mammals, and may be treated in those with the compounds and methods of the present invention.

Thus, the present invention further relates to the use of the compounds according to the invention for the treatment and/or prevention of diseases, especially of the aforementioned diseases.

The present invention further relates to the use of the compounds according to the invention for preparing a pharmaceutical composition for the treatment and/or prevention of diseases, especially of the aforementioned diseases.

The present invention further relates to the use of the compounds according to the invention in a method for the treatment and/or prevention of diseases, especially of the aforementioned diseases.

The present invention further relates to a method for the treatment and/or prevention of diseases, especially of the aforementioned diseases, by using an effective amount of at least one of the compounds according to the invention.

In accordance with another aspect, the present invention covers pharmaceutical combinations, in particular medicaments, comprising at least one compound of general formula (I) of the present invention and at least one or more further active ingredients, in particular for the treatment and/or prevention of diseases, especially of the aforementioned diseases.

Particularly, the present invention covers a pharmaceutical combination, which comprises:
one or more first active ingredients, in particular compounds of general formula (I) as defined supra, and
one or more further active ingredients, in particular for the treatment and/or prevention of diseases, especially of the aforementioned diseases.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known agents for the treatment and/or prevention of diseases, especially of the aforementioned diseases.

In particular, the compounds of the present invention may be used in fixed or separate combination with
antithrombotic agents, for example and preferably from the group of platelet aggregation inhibitors, anticoagulants and profibrinolytic substances;
blood pressure lowering agents, for example and preferably from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics;
antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins).
organic nitrates and NO-donors, for example sodium nitroprusside, nitroglycerin, isosorbide mononitrate, isosorbide dinitrate, molsidomine or SIN-1, and inhalational NO;
compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil, CTP-499 or PF-00489791;
natriuretic peptides, such as for example atrial natriuretic peptide (ANP, anaritide), B-type natriuretic peptide or brain natriuretic peptide (BNP, nesiritide), C-type natriuretic peptide (CNP) or urodilatin;
calcium sensitizers, such as for example and preferably levosimendan;
NO- and heme-independent activators of soluble guanylate cyclase (sGC), for example and with preference the compounds described in WO 01/19355, WO 01/19776, WO 01/19778, WO 01/19780, WO 02/070462 and WO 02/070510;
NO-independent, but heme-dependent stimulators of guanylate cyclase (sGC), for example and with preference the compounds described in WO 00/06568, WO 00/06569, WO 02/42301, WO 03/095451, WO 2011/147809, WO 2012/004258, WO 2012/028647 and WO 2012/059549;
agents, that stimulates the synthesis of cGMP, for example and with preference sGC modulators, for example and with preference riociguat, cinaciguat, vericiguat or BAY 1101042;
inhibitors of human neutrophil elastase (HNE), such as for example sivelestat or DX-890 (reltran);
compounds inhibiting the signal transduction cascade, in particular tyrosine and/or serine/threonine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
compounds influencing the energy metabolism of the heart, such as for example and preferably etomoxir, dichloroacetate, ranolazine or trimetazidine, or full or partial adenosine A1 receptor agonists as GS-9667 (previously known as CVT-3619), capadenoson and neladenoson bialanate (BAY 1067197);
compounds influencing the heart rate, such as for example and preferably ivabradine;
cardiac myosin activators, such as for example and preferably omecamtiv mecarbil (CK-1827452);
anti-inflammatory drugs such as non-steroidal anti-inflammatory drugs (NSAIDs) including acetylsalicylic acid (aspirin), ibuprofen and naproxen, glucocorticoids, such as for example and preferably prednison, prednisolon, methylprednisolon, triamcinolon, dexamethason, beclomethason, betamethason, flunisolid, budesonid or fluticason, 5-aminosalicylic acid derivatives, leukotriene antagonists, TNF-alpha inhibitors and chemokine receptor antagonists such as CCR1, 2 and/or 5 inhibitors;
fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants and profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or enoxaparin.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

Blood pressure lowering agents are preferably to be understood as compounds from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin or tamsulosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII receptor antagonist, for example and preferably losartan, candesartan, valsartan, telmisartan, irbesartan, olmesartan, eprosartan, embursartan or azilsartan.

In a preferred embodiment of the invention, the compounds according to the invention are administered in combination with a vasopeptidase inhibitor or inhibitor of neutral endopeptidase (NEP), such as for example and preferably sacubitril, omapatrilat or AVE-7688.

In a preferred embodiment of the invention, the compounds according to the invention are administered in combination with a dual angiotensin AII receptor antagonist/NEP inhibitor (ARNI), for example and preferably LCZ696.

In a preferred embodiment of the invention, the compounds according to the invention are administered in combination with an ACE inhibitor, for example and preferably enalapril, captopril, lisinopril, ramipril, delapril, fosinopril, quinopril, perindopril, benazepril or trandopril.

In a preferred embodiment of the invention, the compounds according to the invention are administered in combination with an endothelin antagonist, for example and preferably bosentan, darusentan, ambrisentan, tezosentan, sitaxsentan, avosentan, macitentan or atrasentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably finerenone, spironolactone, canrenone, potassium canrenoate, eplerenone, esaxerenone (CS-3150), or apararenone (MT-3995)., In a preferred embodiment of the invention, the compounds according to the invention are administered in combination with a diuretic, such as for example and preferably furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorthalidone, metolazone, quinethazone, acetazolamide, dichlorophenamide, methazolamide, glycerine, isosorbide, mannitol, amiloride or triamterene.

Fat metabolism altering agents are preferably to be understood as compounds from the group of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, for example and preferably dalcetrapib, anacetrapib, BAY 60-5521 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, R-103757, BMS-201038 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, colesolvam, CholestaGel or colestimide.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with HIF-PH inhibitors, by way of example and with preference molidustat or roxadustat.

In a preferred embodiment of the invention, the compounds according to the invention are administered in combination with a CCR2 antagonist, by way of example and with preference CCX-140.

In a preferred embodiment of the invention, the compounds according to the invention are administered in combination with a TNFalpha antagonist, by way of example and with preference adalimumab.

In a preferred embodiment of the invention, the compounds according to the invention are administered in combination with a galectin-3 inhibitor, by way of example and with preference GCS-100.

In a preferred embodiment of the invention, the compounds according to the invention are administered in combination with a BMP-7 agonist, by way of example and with preference THR-184.

In a preferred embodiment of the invention, the compounds according to the invention are administered in combination with a NOX1/4 inhibitor, by way of example and with preference GKT-137831.

In a preferred embodiment of the invention, the compounds according to the invention are administered in combination with a medicament which affects the vitamin D metabolism, by way of example and with preference cholecalciferol or paracalcitol.

In a preferred embodiment of the invention, the compounds according to the invention are administered in combination with a cytostatic agent, by way of example and with preference cyclophosphamide.

In a preferred embodiment of the invention, the compounds according to the invention are administered in combination with an immunosuppressive agent, by way of example and with preference ciclosporin.

In a preferred embodiment of the invention, the compounds according to the invention are administered in combination with a phosphate binder, by way of example and with preference sevelamer or lanthanum carbonate.

In a preferred embodiment of the invention, the compounds according to the invention are administered in combination with a calcimimetic for therapy of hyperparathyroidism.

In a preferred embodiment of the invention, the compounds according to the invention are administered in combination with agents for iron deficit therapy, by way of example and with preference iron products.

In a preferred embodiment of the invention, the compounds according to the invention are administered in combination with agents for the therapy of hyperurikaemia, by way of example and with preference allopurinol or rasburicase.

In a preferred embodiment of the invention, the compounds according to the invention are administered in combination with glycoprotein hormone for the therapy of anaemia, by way of example and with preference erythropoietin.

In a preferred embodiment of the invention, the compounds according to the invention are administered in combination with biologics for immune therapy, by way of example and with preference abatacept, rituximab, eculizumab or belimumab.

In a preferred embodiment of the invention, the compounds according to the invention are administered in combination with Jak inhibitors, by way of example and with preference ruxolitinib, tofacitinib, baricitinib, CYT387, GSK2586184, lestaurtinib, pacritinib (SB1518) or TG101348.

In a preferred embodiment of the invention, the compounds according to the invention are administered in combination with prostacyclin analogs for therapy of microthrombi.

In a preferred embodiment of the invention, the compounds according to the invention are administered in combination with an alkali therapy, by way of example and with preference sodium bicarbonate.

In a preferred embodiment of the invention, the compounds according to the invention are administered in combination with an mTOR inhibitor, by way of example and with preference everolimus or rapamycin.

In a preferred embodiment of the invention, the compounds according to the invention are administered in combination with an NHE3 inhibitor, by way of example and with preference AZD1722.

In a preferred embodiment of the invention, the compounds according to the invention are administered in combination with an eNOS modulator, by way of example and with preference sapropterin.

In a preferred embodiment of the invention, the compounds according to the invention are administered in combination with a CTGF inhibitor, by way of example and with preference FG-3019.

In a preferred embodiment of the invention, the compounds according to the invention are administered in combination with antidiabetics (hypoglycemic or antihyperglycemic agents), such as for example and preferably insulin and derivatives, sulfonylureas such as tolbutamide, carbutamide, acetohexamide, chlorpropamide, glipizide, gliclazide, glibenclamide, glyburide, glibornuride, gliquidone, glisoxepide, glyclopyramide, glimepiride, JB253 and JB558, meglitinides such as repaglinide and nateglinide, biguanides such as metformin and buformin, thiazolidinediones such as rosiglitazone and pioglitazone, alpha-glucosidase inhibitors such as miglitol, acarbose and voglibose, DPP4 inhibitors such as vildagliptin, sitagliptin, saxagliptin, linagliptin, alogliptin, septagliptin and teneligliptin, GLP-1 analogues such as exenatide (also exendin-4, liraglutide, lixisenatide and taspoglutide, or SGLT inhibitors (gliflozins) such as canagliflozin, dapagliflozin and empagliflozin.

In a particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

In a further particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), antiinflammatory agents, immunosuppressive agents, phosphate binders and/or compounds which modulate vitamin D metabolism. Thus, in a further embodiment, the present invention relates to pharmaceutical compositions comprising at least one of the compounds according to the invention and one or more additional therapeutic agents for the treatment and/or prevention of diseases, especially of the aforementioned diseases.

Furthermore, the compounds of the present invention may be utilized, as such or in compositions, in research and diagnostics, or as analytical reference standards and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically acceptable excipients, and to the use thereof for the treatment and/or prevention of diseases, especially of the aforementioned diseases.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Based upon standard laboratory techniques known to evaluate compounds useful for the treatment of cardiovascular and renal disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. Illustratively, the compound of the present invention may be administered parenterally at a dose of about 0.001 mg/kg to about 10 mg/kg, preferably of about 0.01 mg/kg to about 1 mg/kg of body weight. In oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

EXPERIMENTAL SECTION

NMR peak forms are stated as they appear in the spectra, possible higher order effects have not been considered. Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
|---|---|
| br | broad ($^1$H-NMR signal) |
| CI | chemical ionisation |
| d | doublet ($^1$H-NMR signal) |
| dd | doublet of a doublet ($^1$H-NMR signal) |
| DMSO | dimethylsulfoxide |
| ESI | electrospray (ES) ionisation |
| h | hour(s) |
| HPLC | high performance liquid chromatography |
| LC-MS | liquid chromatography mass spectrometry |
| m | multiplet ($^1$H-NMR signal) |
| min | minute(s) |
| MS | mass spectrometry |
| NMR | nuclear magnetic resonance spectroscopy: chemical shifts (δ) are given in ppm. The chemical shifts were corrected by setting the DMSO signal to 2.50 ppm unless otherwise stated. |
| Rt | retention time (as measured either with HPLC or UPLC) in minutes |
| s | singulet ($^1$H-NMR signal) |
| SQD | Single-Quadrupole-Detector |
| t | triplet ($^1$H-NMR signal) |
| THF | tetrahydrofuran |
| UPLC | ultra performance liquid chromatography |

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION

General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera One®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Method 1 (LC/MS):
Instrument: Agilent MS Quad 6150; HPLC: Agilent 1290; Column: Waters Acquity UPLC HSS T3 1.8µ 50×2.1 mm; Eluent A: 1 l Water+0.25 ml 99% formic acid, Eluent B: 1 l Acetonitrile+0.25 ml 99% formic acid; Gradient: 0.0 min 90% A→0.3 min 90% A→1.7 min 5% A→3.0 min 5% A Oven: 50° C.; Flow: 1.20 ml/min; UV-Detection: 205-305 nm.

Method 2 (LC/MS):
Instrument: Waters ACQUITY SQD UPLC System; Column: Waters Acquity UPLC HSS T3 1.8µ 50×1 mm; Eluent A: 1 l Water+0.25 ml 99% formic acid, Eluent B: 1 l Acetonitrile+0.25 ml 99% formic acid; Gradient: 0.0 min 90% A→1.2 min 5% A→2.0 min 5% A Oven: 50° C.; Flow: 0.40 ml/min; UV-Detection: 208-400 nm.

Method 3 (LC/MS):
Instrument MS: Thermo Scientific FT-MS; Geratetyp UHPLC+: Thermo Scientific UltiMate 3000; Column: Waters, HSST3, 2.1×75 mm, C18 1.8 µm; Eluent A: 1 l Water+0.01% Formic acid; Eluent B: 1 l Acetonitrile+0.01% Formic acid; Gradient: 0.0 min 10% B→2.5 min 95% B→3.5 min 95% B; Oven: 50° C.; Flow: 0.90 ml/min; UV-Detection: 210 nm/Optimum Integration Path 210-300 nm.

Method 4 (LC/MS):
Instrument: Waters ACQUITY SQD UPLC System; Column: Waters Acquity UPLC HSS T3 1.8µ 50×1 mm; Eluent A: 1 l Waters+0.25 ml 99% ige Formic acid, Eluent B: 1 l Acetonitrile+0.25 ml 99% formic acid; Gradient: 0.0 min 95% A→6.0 min 5% A→7.5 min 5% A Oven: 50° C.; Flow: 0.35 ml/min; UV-Detection: 210-400 nm.

Method 5 (preparative HPLC):
Column: Chromatorex or Reprosil C18 10 µm; 125×30 mm, Flow: 75 ml/min, Run time: 20 min, Detection at 210 nm, Eluent A: water+0.1% formic acid, Eluent B: acetonitrile+0.1% formic acid; Gradient: 3 min 10% B; 17.5 min: 95% B; 19.5 min 100% B, 20 min 10% B.

EXPERIMENTAL SECTION

Starting Materials And Intermediates

Example 1A 5-(4-Chlorophenyl)-4-[(2R)-3,3,3-trifluoro-2-hydroxypropyl]-2,4-dihydro-3H-1,2,4-triazol-3-one

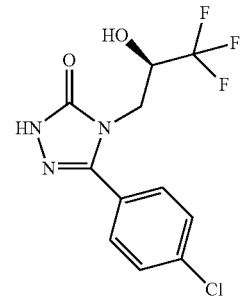 [SMILES: O=c1[nH]nc(-c2ccc(Cl)cc2)n1C[C@@H](O)C(F)(F)F]

A solution of 5-(4-chlorophenyl)-4-(3,3,3-trifluoro-2,2-dihydroxypropyl)-2,4-dihydro-3H-1,2,4-triazol-3-one (synthesis described as Example 4A in WO 2010/105770-A1) (10.0 g, 30.9 mmol), N-[(1R,2R)-2-amino-1,2-diphenylethyl]-4-methylbenzenesulfonamide (56.6 mg, 154 µmol) and 1-methyl-4-(propan-2-yl)benzene-dichlororuthenium (47.3 mg, 77.2 µmol) in ethyl acetate was treated with triethylamine (8.6 ml, 62 mmol) followed by addition of formic acid (5.8 ml, 150 mmol). The resulting mixture was heated under reflux for 3 h and then cooled down to room temperature. The reaction mixture was diluted with hydrochloric acid (70 ml, 1N). The organic phase was washed twice with hydrochloric acid (1N). The aqueous phase was extracted twice with ethyl acetate. The combined organic phases were evaporated. The residue was retaken in methanol (22.5 ml) and the resulting suspension was heated to 60° C. until the solid was completely dissolved. Hydrochloric acid (22.5 ml, 1N) was added and the resulting suspension was heated at 78° C. for 10 min and cooled down to room temperature. The solid was filtered off and dried under vacuum. The solid was retaken in hydrochloric acid (30 ml, 1N), heated at 35° C. The resulting suspension was treated with methanol (30 ml), heated 4 h at 35° C. and filtered off at 35° C. The filtrate solution was evaporated affording 4.9 g (ee=99.6%, 51% th.) of 5-(4-chlorophenyl)-4-[(2R)-3,3,3-trifluoro-2-hydroxypropyl]-2,4-dihydro-3H-1,2,4-triazol-3-one.

LC-MS (Method 3): $R_t$=1.40 min; MS (ESIpos): m/z=308 [M+H]$^+$ $^1$H-NMR (400 MHz, DMSO): δ [ppm]=12.10 (s, 1H), 7.52-7.79 (m, 4H), 6.84 (d, 1H), 3.54-4.52 (m, 3H).

Example 2A

{3-(4-Chlorophenyl)-5-oxo-4-[(2S)-3,3,3-trifluoro-2-hydroxypropyl]-4,5-dihydro-1H-1,2,4-triazol-1-yl}acetonitrile

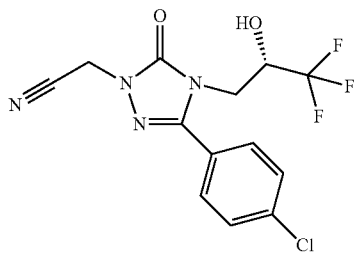 [SMILES: N#CCn1nc(-c2ccc(Cl)cc2)n(C[C@H](O)C(F)(F)F)c1=O]

In a 2 L reaction vessel, 100 g (273 mmol) of {3-(4-chlorophenyl)-5-oxo-4-[(2S)-3,3,3-trifluoro-2-hydroxypropyl]-4,5-dihydro-1H-1,2,4-triazol-1-yl}acetic acid (synthesis described as Example 8A in WO 2010/105770-A1), 43.3 g (547 mmol) of pyridine and 33 mg (0.3 mmol) of 4-dimethylaminopyridine were dissolved in 300 ml THF. The resulting solution was treated at 5° C. with 52.8 g (438 mmol) of 2,2-dimethylpropanoylchloride over 15 minutes and the resulting mixture was stirred at room temperature for 2.5 hours. After cooling to 0° C., 183 ml of 28% aqueous ammonia solution was added over 1 h while the solution temperature was kept between 10° C. and 20° C. and at the resulting mixture then stirred at 5° C. for an additional time period of 1 h. 500 ml methyl tert-butylether and 300 ml 20% aqueous citric acid were then added while keeping the internal temperature between 10° C. and 20° C. The phases were the separated and the organic phase was washed with 300 ml of 20% aqueous citric acid followed by 300 ml saturated aqueous sodium hydrogencarbonate solution and finally with 300 ml of 10% aqueous sodium chloride solution. The organic phase was evaporated at 60° C. under reduced pressure until an oily residue was obtained. 300 ml THF was then added and the solution was evaporated again until an oily solution was obtained. This operation was repeated a second time. The oil residue was retaken in 360 ml THF and treated with 172 g (820 mmol) trifluoroacetic acid anhydride over 20 min at a temperature between 10° C. and 20° C. The resulting solution was then stirred at room temperature for 1 h. 720 ml 4-methyl-2-pentanone and 650 ml 7.5% aqueous sodium hydroxide solution were added at a temperature between 10° C. and 20° C. Finally the pH-value was adjusted to pH=9.5 using 7.5% aqueous sodium hydroxide solution. After phase separation, the organic phase was washed twice with 450 ml 10% aqueous sodium chloride solution. The organic phase was evaporated at a temperature of 80° C. under reduced pressure while 1200 ml n-heptane was added. The formed suspension was cooled to 20° C. and a solid formed which was filtered off and washed with 200 ml n-heptane and then dried under reduced pressure (50° C., 30 mbar) affording 88 g (93% of th.) of {3-(4-chlorophenyl)-5-oxo-4-[(2 S)-3,3,3-trifluoro-2-hydroxypropyl]-4,5-dihydro-1H-1,2,4-triazol-1-yl}acetonitrile as a solid.

$^1$H-NMR (400 MHz, DMSO-d6): δ [ppm]=7.78 (d, 2H), 7.55 (d, 2H), 6.91 (d, 1H), 5.17 (s, 2H), 4.34-4.23 (m, 1 H), 3.98 (dd, 1H), 3.81 (dd, 1H).

Example 3A

{3-(4-Chlorophenyl)-5-oxo-4-[(2R)-3,3,3-trifluoro-2-hydroxypropyl]-4,5-dihydro-1H-1,2,4-triazol-1-yl}acetonitrile

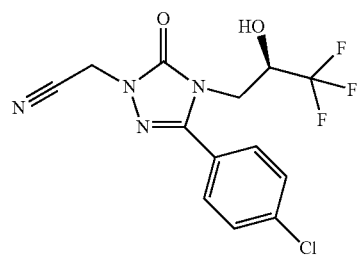 [SMILES: N#CCn1nc(-c2ccc(Cl)cc2)n(C[C@@H](O)C(F)(F)F)c1=O]

A solution of 40 g (130 mmol) 5-(4-Chlorophenyl)-4-[(2R)-3,3,3-trifluor-2-hydroxypropyl]-2,4-dihydro-3H-1,2,4-triazol-3-one (Example 1A) in 400 ml methylisobutyl ketone was treated with 17.9 g (143 mmol) bromoacetonitrile and 53.9 g (390 mmol) potassium carbonate and stirred for 4 hours at 60° C. After cooling to 20° C., 200 ml water was added and the mixture was stirred for 10 min. After phase separation, the organic phase was washed with 200 ml water. The organic phase was evaporated at 80° C. under reduced pressure while 300 ml n-heptane was added. The formed suspension was cooled to 20° C. and a solid formed which was filtered off and washed with 50 ml n-heptane and then dried under reduced pressure (50° C., 30 mbar) affording 25.2 g (56% of th.) of {3-(4-chlorophenyl)-5-oxo-4-[(2R)-3,3,3-trifluoro-2-hydroxypropyl]-4,5-dihydro-1H-1,2,4-triazol-1-yl}acetonitrile.

$^1$H-NMR (400 MHz, DMSO-d6): δ [ppm]=7.78 (d, 2H), 7.65 (d, 2H), 6.91 (d, 1H), 5.17 (s, 2H), 4.34-4.23 (m, 1H), 3.98 (dd, 1H), 3.81 (dd, 1H).

Example 4A

Methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate

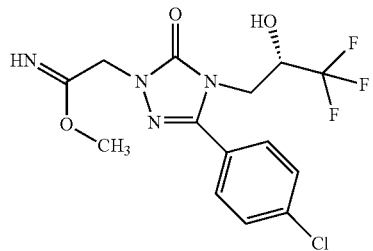 [SMILES: COC(=N)Cn1nc(-c2ccc(Cl)cc2)n(C[C@H](O)C(F)(F)F)c1=O]

In a 4 L reaction vessel, 200 g (576.9 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (Example 2A) in 1600 ml methanol was treated with 5.2 g (28 mmol) sodium methanolate (30% in methanol) and the resulting mixture was stirred at 50° C. for 2.5 hours. The solution was then evaporated at 50° C. under reduced pressure until an oily solution was obtained. 2000 ml methyl tert-butylether was added and the solution was concentrated until a volume of 800 ml was achieved. 3000 ml n-heptane was then added and a suspension was formed. After cooling at 20° C., the solid was filtered and washed with 500 ml n-heptane and then dried under reduced pressure (50° C., 30 mbar) affording 175 g (80% of th.) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate as a solid.

$^1$H-NMR (400 MHz, DMSO-d6): δ [ppm]=8.01 (s, 1H), 7.78 (d, 2H), 7.62 (d, 2H), 6.93 (br. s, 1H), 4.50 (s, 2 H), 4.35-4.23 (m, 1 H), 3.96 (dd, 1H), 3.81 (dd, 1H), 3.67 (s, 3 H).

Example 5A

Methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate

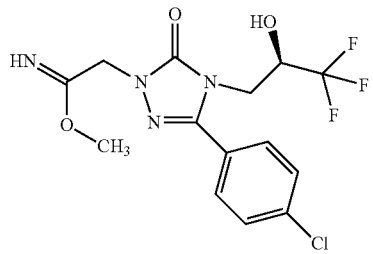 [SMILES: COC(=N)Cn1nc(-c2ccc(Cl)cc2)n(C[C@@H](O)C(F)(F)F)c1=O]

A solution 8.58 g (24.7 mmol) of {3-(4-chlorophenyl)-5-oxo-4-[(2R)-3,3,3-trifluoro-2-hydroxypropyl]-4,5-dihydro-1H-1,2,4-triazol-1-yl}acetonitrile (Example 3A) in methanol (43 ml) was treated with 229 μl (1.24 mmol) of a sodium methoxide solution (30% in methanol). The resulting mixture was stirred overnight at room temperature and then evaporated affording 9.31 g (99% of th.) of the title compound.

$^1$H NMR (DMSO-d$_6$, 400 MHz): δ [ppm]=8.01 (s, 1H), 7.81-7.58 (m, 4H), 7.00-6.84 (m, 1H), 4.50 (s, 2H), 4.40-4.23 (m, 1H), 4.04-3.74 (m, 2H), 3.66 (s, 3H).

Example 6A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxylate

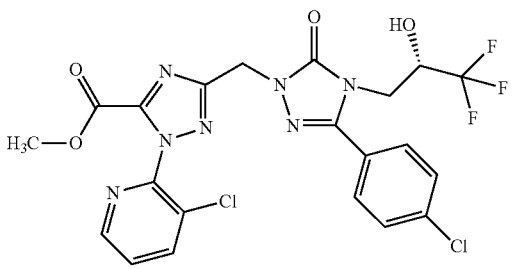 [SMILES: COC(=O)c1nc(Cn2nc(-c3ccc(Cl)cc3)n(C[C@H](O)C(F)(F)F)c2=O)nn1-c1ncccc1Cl]

A solution of 150 mg of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (26.4 mmol) in 3 ml THF was cooled to 0° C. and then treated with 58.2 mg (0.48 mmol) methyl chlorooxoacetate and 275 μL, (1.58 mmol) N,N-diisopropylethylamine. The resulting mixture was warmed up to room temperature and stirred for 1 h and cooled again to 0° C. 62.6 mg (0.436 mmol) 3-chloro-2-hydrazinopyridine were then added and the reaction mixture was warmed up to room temperature and then stirred for 1 h, followed by 1 h at 120° C. in a sealed vial under microwave irradiation. The crude product was purified by preparative HPLC (Method 5). Lyophilisation of the product containing fractions afforded 25.3 mg (11% of th.) of the title compound.

LC-MS (Method 3): R$_t$=1.82 min; MS(ESIpos): m/z=558.1[M+H]$^+$ $^1$H NMR (DMSO-d$_6$, 400 MHz): δ=8.70-8.24 (m, 2H), 7.89-7.56 (m, 5H), 6.92 (d, 1H), 5.22 (s, 2H), 4.46-4.20 (m, 1H), 3.79 (s, 5H).

Example 7A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxylate

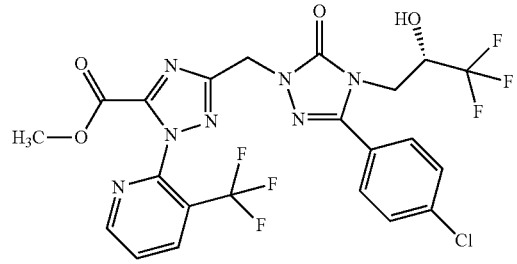 [SMILES: COC(=O)c1nc(Cn2nc(-c3ccc(Cl)cc3)n(C[C@H](O)C(F)(F)F)c2=O)nn1-c1ncccc1C(F)(F)F]

A solution of 1.0 g of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (2.64 mmol) in 20 ml 1,4-dioxane was cooled to 10° C. and then treated with 388 mg (3.17 mmol) methyl chlorooxoacetate and 0.55 mL (3.18 mmol) N,N-diisopropylethylamine. The resulting mixture was then stirred for 30 min. A prestirred solution of 1.10 g (3.17 mmol) 2-hydrazino-3-(trifluoromethyl)pyridine (4-methylbenzenesulfonate salt 1:1), 0.65 mL (3.72 mmol) N,N-diisopropylethylamine and 506 mg (3.19 mmol) anhydrous copper(II) sulfate in 10 mL 1,4-dioxane were added to the reaction mixture and the resulting mixture was then stirred overnight at room temperature. Water was then added and the aqueous phase was extracted with ethyl acetate, the combined organic phases were washed with aqueous sodium chloride solution, dried over magnesium sulfate and evaporated in vacuo affording 777 mg (50% of th.) of the title compound as a solid.

LC-MS (Method 2): R$_t$=1.00 min; MS(ESIpos): m/z=592.6 [M+H]$^+$ $^1$H NMR (DMSO-d$_6$, 400 MHz): δ=8.93 (d, 1H), 8.60 (dd, 1H), 7.98 (dd, 1H), 7.75 (d, 2H), 7.67-7.57 (m, 2H), 6.91 (d, 1H), 5.22 (s, 2H), 4.37-4.22 (m, 1H), 4.10-3.97 (m, 1H), 3.85 (dd, 1H), 3.77 (s, 3H).

Example 8A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethoxy)pyridin-2-yl]-1H-1,2,4-triazole-5-carboxylate

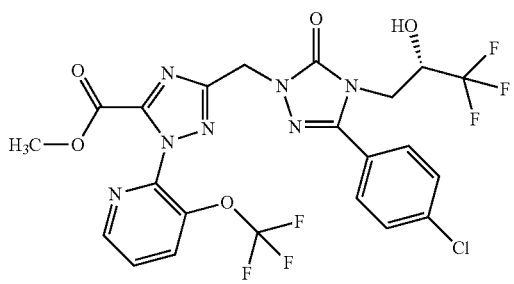 [SMILES: COC(=O)c1nc(Cn2nc(-c3ccc(Cl)cc3)n(C[C@H](O)C(F)(F)F)c2=O)nn1-c1ncccc1OC(F)(F)F]

A solution of 150 mg of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (0.40 mmol) in 3 ml THF was cooled to 0° C. and treated with 58 mg (0.48 mmol) methyl chlorooxoacetate and 275 µL (1.58 mmol) N,N-diisopropylethylamine. The resulting mixture was warmed up to room temperature and then stirred for 1 h and thereafter cooled again to 0° C. 159 mg (0.44 mmol) 2-hydrazino-3-(trifluoromethoxy)pyridine (4-methylbenzenesulfonate salt 1:1) were then added and the reaction mixture was then warmed up to room temperature and stirred for 1 h, followed by 1 h at 120° C. in a sealed vial under microwave irradiation. The crude product was purified by preparative HPLC (Method 5). Lyophilisation of the product containing fractions afforded 51.5 mg (21% of th.) of the title compound as a solid.

LC-MS (Method 2): $R_t$=1.02 min; MS(ESIpos): m/z=608.1 [M+H]$^+$.

Example 9A

Methyl 1-(3-bromopyridin-2-yl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazole-5-carboxylate

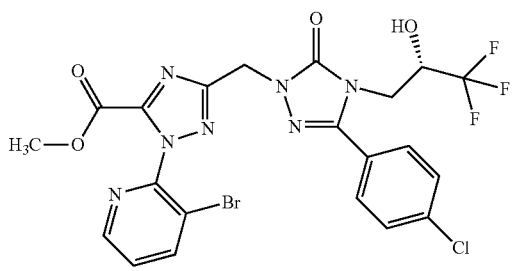

A solution of 1.0 g of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (2.64 mmol) in 20 ml 1,4-dioxane was cooled to 10° C. and then treated with 388 mg (3.17 mmol) methyl chlorooxoacetate and 0.55 mL (3.18 mmol) N,N-diisopropylethylamine. The resulting mixture was stirred for 30 min. A prestirred solution of 595 mg (3.17 mmol) 3-bromo-2-hydrazinopyridine and 506 mg (3.19 mmol) anhydrous copper(II) sulfate in 10 mL of 1,4-dioxane was then added to the reaction mixture and the resulting mixture was stirred overnight at room temperature. Water was then added and the aqueous phase was extracted with ethyl acetate, the combined organic phases were washed with aqueous sodium chloride solution, dried over magnesium sulfate and evaporated in vacuo. The crude product was purified by column chromatography (silica gel, cyclohexane/EtOAc 12%→100%), affording 696 mg (44% of th.) of the title compound.

LC-MS (Method 3): $R_t$=1.82 min; MS(ESIpos): m/z=602.0 [M+H]$^+$.

$^1$H NMR (DMSO-d$_6$, 400 MHz): δ=8.63 (dd, 1H), 8.45 (dd, 1H), 7.76 (d, 2H), 7.66 (dd, 1H), 7.62 (d, 2H), 6.92 (d, 1H), 5.22 (s, 2H), 4.38-4.25 (m, 1H), 4.09-3.96 (m, 1H), 3.85 (dd, 1H), 3.79 (s, 3H).

Example 10A

Ethyl 2-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]nicotinate

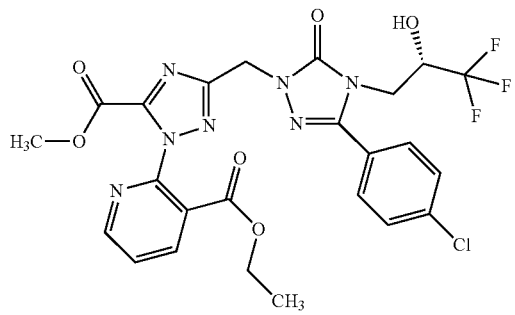 [SMILES: CCOC(=O)c1cccnc1-n1nc(Cn2nc(-c3ccc(Cl)cc3)n(C[C@H](O)C(F)(F)F)c2=O)nc1C(=O)OC]

A solution of 2.35 g of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (26.19 mmol) in 47 ml 1,4-dioxane was cooled to 10° C. and then treated with 910 mg (7.41 mmol) methyl chlorooxoacetate and 1.20 mL (7.41 mmol) N,N-diisopropylethylamine. The resulting mixture was then stirred for 30 min. A prestirred solution of 1.87 g (7.41 mmol) ethyl 2-hydrazinonicotinate and 1.45 mg (9.10 mmol) anhydrous copper(II) sulfate in 23 mL 1,4-dioxane was then added to the reaction mixture and the resulting mixture was stirred for 96 h at room temperature. The solvent was removed in vacuo and the crude product was purified by column chromatography (silica gel, dichloromethane/methanol, 92/8), affording 833 mg (23% of th.) of the title compound as a solid.

LC-MS (Method 2): $R_t$=0.98 min; MS(ESIpos): m/z=596.1 [M+H]$^+$ $^1$H NMR (DMSO-d$_6$, 400 MHz): δb=8.82 (dd, 1H), 8.51 (dd, 1H), 7.85 (dd, 1H), 7.75 (d, 2H), 7.65-7.57 (m, 2H), 6.91 (d, 1H), 5.17 (s, 2H), 4.38-4.24 (m, 1H), 4.13-3.96 (m, 3H), 3.85 (dd, 1H), 3.77 (s, 3H), 0.97 (t, 3H).

Example 11A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(4-chloropyridin-3-yl)-1H-1,2,4-triazole-5-carboxylate

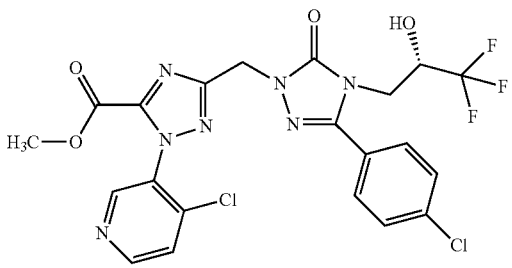 [SMILES: COC(=O)c1nc(Cn2nc(-c3ccc(Cl)cc3)n(C[C@H](O)C(F)(F)F)c2=O)nn1-c1cnccc1Cl]

A solution of 1.0 g of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (2.64 mmol) in 18 ml THF was cooled to 0° C. and treated with 388 mg (3.17 mmol) methyl chlorooxoacetate and 1.06 mL (6.07 mmol) N,N-diisopropylethylamine. The resulting mixture was warmed up to room temperature and then stirred for 1 h and cooled again to 0° C. 523 mg (2.90 mmol) 4-chloro-3-hydrazinopyridine (hydrochloride salt 1:1) was added and the reaction mixture was warmed up to room temperature and then stirred for 1 h, followed by 1 h at 120° C. in a sealed vial under microwave irradiation. The crude product was purified by column chromatography (silica gel, cyclohexane/EtOAc, gradient), affording 1.03 g (66% of th.) of the title compound as a solid.

LC-MS (Method 2): $R_t$=1.00 min; MS(ESIpos): m/z=558.2 [M+H]$^+$ $^1$H NMR (DMSO-d$_6$, 400 MHz): δ=9.00-8.62 (m, 2H), 7.96-7.55 (m, 5H), 6.91 (d, 1H), 5.21 (s, 2H), 4.42-4.21 (m, 1H), 4.11-3.66 (m, 5H).

Example 12A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[4-(trifluoromethyl)pyridin-3-yl]-1H-1,2,4-triazole-5-carboxylate

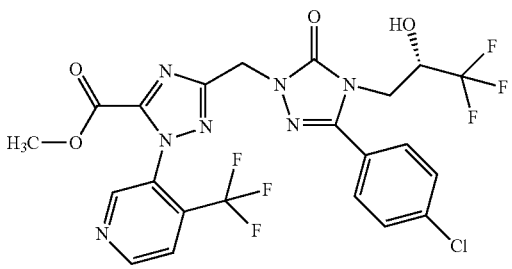 [SMILES: COC(=O)c1nc(Cn2nc(-c3ccc(Cl)cc3)n(C[C@H](O)C(F)(F)F)c2=O)nn1-c1cnccc1C(F)(F)F]

A solution of 150 mg of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (0.40 mmol) in 3 ml THF was cooled to 0° C. and treated with 53 mg (0.44 mmol) methyl chlorooxoacetate and 75 μL, (0.44 mmol) N,N-diisopropylethylamine. The resulting mixture was stirred for 30 min at 0° C. 77 mg (0.44 mmol) 3-hydrazino-4-(trifluoromethyl)pyridine was added and the reaction mixture was then warmed up to room temperature and stirred for 1 h, followed by 1 h at 100° C. in a sealed vial under microwave irradiation. The crude product was purified by preparative HPLC (Method 5). Lyophilisation of the product containing fractions afforded 104 mg (41% of th.) of the title compound as a solid LC-MS (Method 3): $R_t$=1.84 min; MS(ESIpos): m/z=592.1 [M+H]$^+$ $^1$H NMR (DMSO-d$_6$, 400 MHz): δ=9.12-9.04 (m, 2H), 8.07 (d, 1H), 7.75 (d, 2H), 7.63 (d, 2H), 6.91 (d, 1H), 5.20 (d, 2H), 4.39-4.20 (br m, 1H), 4.05-3.98 (m, 1H), 3.86 (dd, 1H), 3.77 (s, 3H).

Example 13A

Ethyl 3-[3-({3-(4-chlorophenyl)-5-oxo-4-[(2S)-3,3,3-trifluoro-2-hydroxypropyl]-4,5-dihydro-1H-1,2,4-triazol-1-yl}methyl)-5-(methoxycarbonyl)-1H-1,2,4-triazol-1-yl]isonicotinate

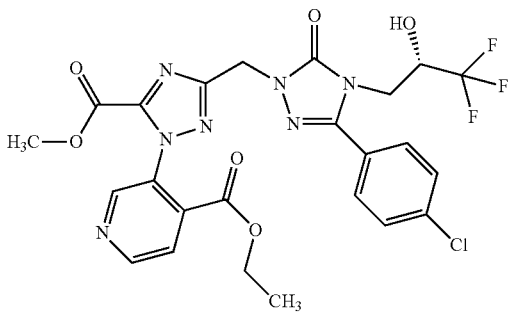 [SMILES: CCOC(=O)c1ccncc1-n1nc(Cn2nc(-c3ccc(Cl)cc3)n(C[C@H](O)C(F)(F)F)c2=O)nc1C(=O)OC]

A solution of 500 mg of methyl-2-{3-(4-chlorophenyl)-5-oxo-4-[(2S)-3,3,3-trifluor-2-hydroxypropyl]-4,5-dihydro-1H-1,2,4-triazol-1-yl}ethanimidate (Example 4A) (1.32 mmol) in 10 ml THF was cooled to 0° C. and treated with 178 mg (1.45 mmol) methyl chlorooxoacetate and 252 μL (1.45 mmol) N,N-diisopropylethylamine. The resulting mixture was stirred for 30 min at 0° C. 309 mg (1.45 mmol) ethyl 3-hydrazinoisonicotinate were then added and the reaction mixture was warmed up to room temperature and then stirred for 16 h, followed by heating to reflux for 16 h. The crude product was purified by preparative HPLC (Method 5). Lyophilisation of the product containing fractions afforded 416 mg (26% of th.) of the title compound.

LC-MS (Method 3): $R_t$=1.83 min; MS(ESIpos): m/z=596.1 [M+H]$^+$ $^1$H NMR (DMSO-d$_6$, 400 MHz): δ=9.00-8.90 (m, 2H), 7.96 (d, 1H), 7.75 (d, 2H), 7.67-7.60 (m, 2H), 6.91 (d, 1H), 5.17 (s, 2H), 4.37-4.22 (m, 1H), 4.09-3.97 (m, 3H), 3.86 (dd, 1H), 3.76 (s, 3H), 0.93 (t, 3H).

Example 14A

Methyl 3-({3-(4-chlorophenyl)-5-oxo-4-[(2R)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxylate

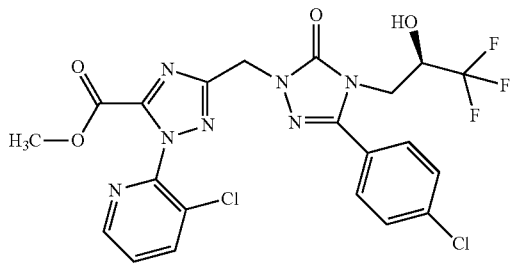 [SMILES: COC(=O)c1nc(Cn2nc(-c3ccc(Cl)cc3)n(C[C@@H](O)C(F)(F)F)c2=O)nn1-c1ncccc1Cl]

A solution of 546 mg of methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate (Example 5A) (1.44 mmol) in 10 ml THF was cooled to 0° C. and treated with 194 mg (1.59 mmol) methyl chlorooxoacetate and 277 µL, (1.59 mmol) N,N-diisopropylethylamine. The resulting mixture was stirred for 30 min at 0° C. 227 mg (1.59 mmol) 3-chloro-2-hydrazinopyridine were then added and the reaction mixture was warmed up to room temperature and then stirred for 1 h, followed by 1 h at 120° C. in a sealed vial under microwave irradiation and further 36 h at room temperature. The reaction mixture was then treated with Methanol/water and purified by preparative HPLC (Method 5). Lyophilisation of the product containing fractions afforded 121 mg (14% of th.) of the title compound as a solid.

LC-MS (Method 3): $R_t$=1.85 min; MS(ESIpos): m/z=558.1 [M+H]$^+$ $^1$H NMR (DMSO-d$_6$, 400 MHz): δ=8.81-8.18 (m, 2H), 7.92-7.48 (m, 5H), 6.91 (d, 1H), 5.22 (s, 2H), 4.44-4.16 (m, 1H), 3.79 (s, 5H).

Example 15A

Methyl 3-({3-(4-chlorophenyl)-5-oxo-4-[(2R)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxylate

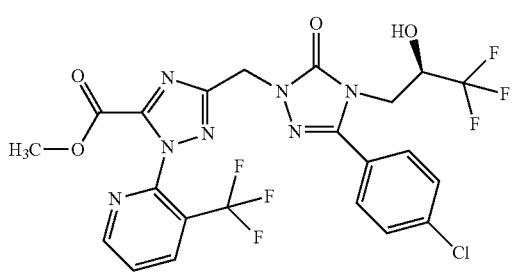 [SMILES: COC(=O)c1nc(Cn2nc(-c3ccc(Cl)cc3)n(C[C@@H](O)C(F)(F)F)c2=O)nn1-c1ncccc1C(F)(F)F]

A solution of 340 mg of methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate (Example 5A) (898 µmot) in 8 ml 1,4-dioxane was cooled to 10° C. and treated with 132 mg (1.08 mmol) methyl chlorooxoacetate and 305 µL, (2.33 mmol) N,N-diisopropylethylamine. The resulting mixture was stirred for 30 min. A prestirred solution of 376 mg (1.08 mmol) 2-hydrazino-3-(trifluoromethyl)pyridine (4-methylbenzenesulfonate salt 1:1) and 172 mg (1.08 mmol) anhydrous copper(II) sulfate in 4 mL 1,4-dioxane was then added to the reaction mixture and the resulting mixture was stirred for 16 h at room temperature. The solvent was removed in vacuo and the crude product was dissolved in EtOAc and washed with a solution of 10% EDTA in water (four times repeated) followed by water and aqueous saturated sodium chloride solution. After drying over magnesium sulfate the volatiles were removed and the crude product obtained was purified by preparative HPLC (Method 5). Lyophilisation of the product containing fractions afforded 167 mg (31% of th.) of the title compound as a solid.

LC-MS (Method 3): $R_t$=1.88 min; MS(ESIpos): m/z=592.1 [M+H]$^+$ $^1$H NMR (DMSO-d$_6$, 400 MHz): δ=8.93 (d, 1H), 8.60 (dd, 1H), 7.98 (dd, 1H), 7.80-7.67 (m, 2H), 7.67-7.58 (m, 2H), 6.91 (d, 1H), 5.28-5.13 (m, 2H), 4.37-4.24 (m, 1H), 4.06-3.95 (m, 1H), 3.85 (dd, 1H), 3.77 (s, 3H).

Example 16A

Methyl 3-({3-(4-chlorophenyl)-5-oxo-4-[(2R)-3,3,3-trifluoro-2-hydroxypropyl]-4,5-dihydro-1H-1,2,4-triazol-1-yl}methyl)-1-(4-chloropyridin-3-yl)-1H-1,2,4-triazole-5-carboxylate

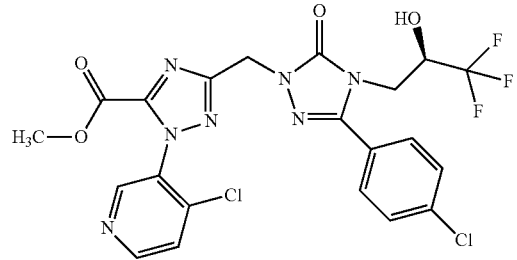 [SMILES: COC(=O)c1nc(Cn2nc(-c3ccc(Cl)cc3)n(C[C@@H](O)C(F)(F)F)c2=O)nn1-c1cnccc1Cl]

A solution of 330 mg of methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate (Example 5A) (871 µmol) in 6.6 ml THF was cooled to 0° C. and treated with 117 mg (958 µmol) methyl chlorooxoacetate and 166 µL (958 µmol) N,N-diisopropylethylamine. The resulting mixture was then stirred for 30 min. at 0° C. 166 µL (958 µmol) N,N-diisopropylethylamine and 172 mg (958 µmol) 4-chloro-3-hydrazinopyridine (hydrochloride salt 1:1) was added and the resulting reaction mixture was warmed up to room temperature and then stirred for 16 h, followed by further 1 h at 100° C. in a sealed vial under microwave irradiation The crude product was purified by preparative HPLC (Method 5). Lyophilisation of the product containing fractions afforded 126 mg (26% of th.) of the title compound as a solid LC-MS (Method 3): $R_t$=1.75 min; MS(ESIpos): m/z=558.1 [M+H]$^+$ $^1$H NMR (DMSO-d$_6$, 400 MHz): δ=8.86 (s, 1H), 8.75 (d, 1H), 7.89 (d, 1H), 7.80-7.73 (m, 2H), 7.65-7.60 (m, 2H), 6.91 (d, 1H), 5.21 (s, 2H), 4.36-4.24 (m, 1H), 4.08-3.99 (m, 1H), 3.86 (dd, 1H), 3.79 (s, 3H).

Example 17A

Methyl 3-({3-(4-chlorophenyl)-5-oxo-4-[(2R)-3,3,3-trifluoro-2-hydroxypropyl]-4,5-dihydro-1H-1,2,4-triazol-1-yl}methyl)-1-[4-(trifluoromethyl)pyridin-3-yl]-1H-1,2,4-triazole-5-carboxylate

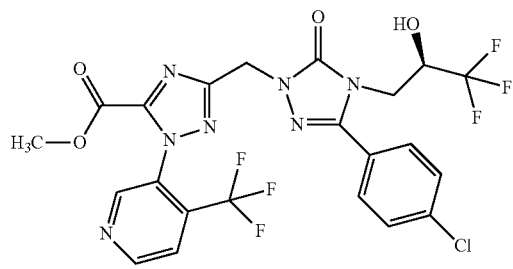 [SMILES: COC(=O)c1nc(Cn2nc(-c3ccc(Cl)cc3)n(C[C@@H](O)C(F)(F)F)c2=O)nn1-c1cnccc1C(F)(F)F]

A solution of 350 mg of methyl-2-{3-(4-chlorophenyl)-5-oxo-4-[(2R)-3,3,3-trifluor-2-hydroxypropyl]-4,5-dihydro-1H-1,2,4-triazol-1-yl}ethanimidate (Example 5A) (0.924 mmol) in 7.0 ml THF was cooled to 0° C. and treated with 124 mg (1.02 mmol) methyl chlorooxoacetate and 177 µL, (1.102 mmol) N,N-diisopropylethylamine. The resulting mixture was stirred for 30 min at 0° C. 180 mg (1.02 mmol) 3-hydrazino-4-(trifluoromethyl)pyridine was added and the reaction mixture was warmed up to room temperature and stirred for 16 h, followed by 1 h at 100° C. in a sealed vial under microwave irradiation The crude product was purified by preparative HPLC (Method 5). Lyophilisation of the product containing fractions afforded 125 mg (23% of th.) of the title compound as a solid LC-MS (Method 3): $R_t$=1.85 min; MS(ESIpos): m/z=592.1 [M+H]$^+$ $^1$H NMR (DMSO-d$_6$, 400 MHz): δ=9.09 (d, 1H), 9.07 (s, 1H), 8.07 (d, 1H), 7.77-7.73 (m, 2H), 7.65-7.61 (m, 2H), 6.91 (d, 1H), 5.20 (d, 2H), 4.39-4.20 (br m, 1H), 4.04-3.98 (m, 1H), 3.86 (dd, 1H), 3.77 (s, 3H).

EXPERIMENTAL SECTION

Examples

Example 1

3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide

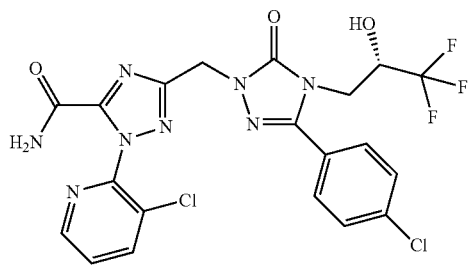 [SMILES: NC(=O)c1nc(Cn2nc(-c3ccc(Cl)cc3)n(C[C@H](O)C(F)(F)F)c2=O)nn1-c1ncccc1Cl]

5.1 g methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxylate (Example 6A, 9.134 mmol) was dissolved in 42.5 mL of an ammonia solution (7N in methanol, 297 mmol). The resulting mixture was stirred for 2 h at room temperature. The solution was then poured on ice and the mixture stirred for 10 min. The precipitate was filtered off and washed with water, which afforded 3.5 g of crude product. The aqueous phase was extraced with ethyl acetate. The organic phase was dried over magnesium sulfate, filtered and the solvent was removed in vacuo. The crude product was purified by flash chromatography (silica gel, dichloromethane/methanol, 97/3), affording 4.00 g (81% of th.) of the title compound as a solid.

LC-MS (Method 3): $R_t$=1.62 min; MS(ESIpos): m/z=543.1 [M+H]$^+$ $^1$H NMR (DMSO-d$_6$, 400 MHz): b=8.55 (dd, 1H), 8.39 (s, 1H), 8.25 (dd, 1H), 8.00 (s, 1H), 7.76 (d, 2H), 7.69 (dd, 1H), 7.62 (d, 2H), 6.90 (d, 1H), 5.18 (d, 2H), 4.36-4.23 (m, 1H), 4.06-3.97 (m, 1H), 3.85 (dd, 1H).

Example 2

3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide

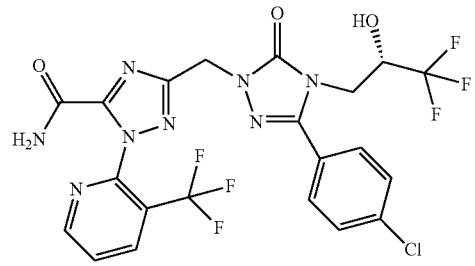 [SMILES: NC(=O)c1nc(Cn2nc(-c3ccc(Cl)cc3)n(C[C@H](O)C(F)(F)F)c2=O)nn1-c1ncccc1C(F)(F)F]

1.80 g methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxylate (Example 7A, 3.04 mmol) was dissolved in 10.0 mL of an ammonia solution (7N in methanol, 70.0 mmol). The resulting mixture was stirred for 1 h at room temperature. The solvent was removed in vacuo and the crude product was purified by preparative HPLC (Method 5). Lyophilisation of the product containing fractions afforded 1.49 g (85% of th.) of the title compound as a solid.

LC-MS (Method 1): $R_t$=1.20 min; MS(ESIpos): m/z=577 [M+H]$^+$ $^1$H NMR (DMSO-d$_6$, 400 MHz): δ=8.87 (d, 1H), 8.51 (d, 1H), 8.39 (s, 1H), 7.99 (s, 1H), 7.90 (dd, 1H), 7.82-7.68 (m, 2H), 7.63 (d, 2H), 6.90 (s, 1H), 5.22-5.07 (m, 2H), 4.39-4.20 (br m, 1H), 4.16-3.94 (m, 1H), 3.85 (dd, 1H).

Example 3

3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethoxy)pyridin-2-yl]-1H-1,2,4-triazole-5-carboxamide

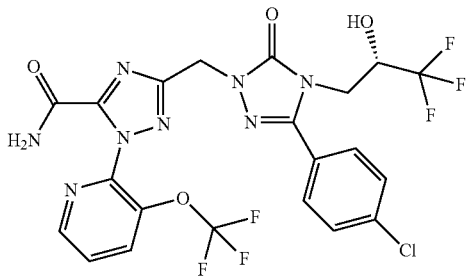 [SMILES: NC(=O)c1nc(Cn2nc(-c3ccc(Cl)cc3)n(C[C@H](O)C(F)(F)F)c2=O)nn1-c1ncccc1OC(F)(F)F]

51.0 mg Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethoxy)pyridin-2-yl]-1H-1,2,4-triazole-5-carboxylate (Example 8A, 84 µmol) was dissolved in 5.0 mL of an ammonia solution (7N in methanol, 35.0 mmol). The resulting mixture was stirred for 1 h at room temperature. The solvent was removed in vacuo and the crude product was purified by preparative HPLC (Method 5). Lyophilisation of the product containing fractions afforded 44.2 mg (89% of th.) of the title compound as a solid.

LC-MS (Method 3): $R_t$=1.69 min; MS(ESIpos): m/z=593.1 [M+H]$^+$ $^1$H NMR (DMSO-$d_6$, 400 MHz): δ=8.71-7.53 (m, 9H), 6.90 (d, 1H), 5.17 (d, 2H), 4.42-4.17 (m, 1H), 4.08-3.73 (m, 2H).

Example 4

1-(3-Bromopyridin-2-yl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazole-5-carboxamide

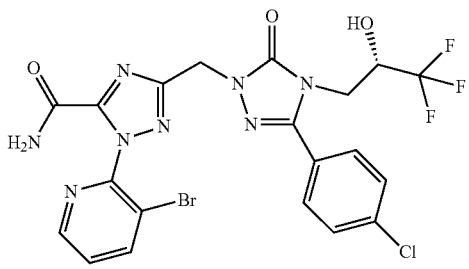 [SMILES: NC(=O)c1nc(Cn2nc(-c3ccc(Cl)cc3)n(C[C@H](O)C(F)(F)F)c2=O)nn1-c1ncccc1Br]

100 mg methyl 1-(3-bromopyridin-2-yl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazole-5-carboxylate (Example 9A, 0.166 mmol) was dissolved in 10.0 mL of an ammonia solution (7N in methanol, 70.0 mmol). The resulting mixture was stirred for 1 h at room temperature. The solvent was removed in vacuo and the crude product was purified by preparative HPLC (Method 5). Lyophilisation of the product containing fractions afforded 83.1 mg (85% of th.) of the title compound as a solid.

LC-MS (Method 2): $R_t$=0.91 min; MS(ESIpos): m/z=587.0 [M+H]$^+$ $^1$H NMR (DMSO-$d_6$, 400 MHz): δ=8.57 (dd, 1H), 8.36 (dd, 2H), 7.98 (s, 1H), 7.80-7.73 (m, 2H), 7.62 (d, 2H), 7.60-7.56 (m, 1H), 6.92 (d, 1H), 5.17 (d, 2H), 4.41-4.19 (m, 1H), 4.11-3.95 (m, 1H), 3.85 (dd, 1H).

Example 5

Ethyl 2-[5-carbamoyl-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]nicotinate

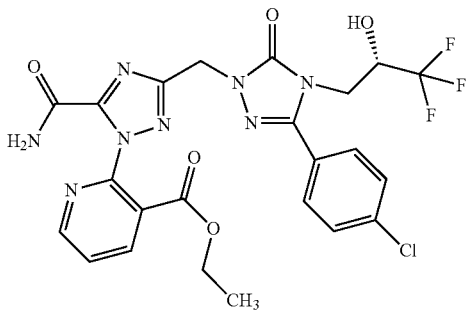 [SMILES: CCOC(=O)c1cccnc1-n1nc(Cn2nc(-c3ccc(Cl)cc3)n(C[C@H](O)C(F)(F)F)c2=O)nc1C(N)=O]

50.0 mg Example 10A (84 µmol) was dissolved in 1.25 mL of an ammonia solution (7N in methanol, 0.175 mmol). The resulting mixture was stirred for 1 h at room temperature. The solvent was removed in vacuo and the crude product was purified by preparative HPLC (Method 5). Lyophilisation of the product containing fractions afforded 27.8 mg (57% of th.) of the title compound as a solid.

LC-MS (Method 1): $R_t$=1.16 min; MS(ESIpos): m/z=581.0 [M+H]$^+$ $^1$H NMR (DMSO-$d_6$, 400 MHz): δ=8.76 (dd, 1H), 8.46 (dd, 1H), 8.29 (s, 1H), 7.90 (s, 1H), 7.83-7.77 (m, 1H), 7.77-7.70 (m, 2H), 7.68-7.57 (m, 2H), 6.90 (d, 1H), 5.14 (s, 2H), 4.35-4.23 (m, 1H), 4.06-3.97 (m, 3H), 3.85 (dd, 1H), 0.97 (t, 3H).

Example 6

3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(4-chloropyridin-3-yl)-1H-1,2,4-triazole-5-carboxamide

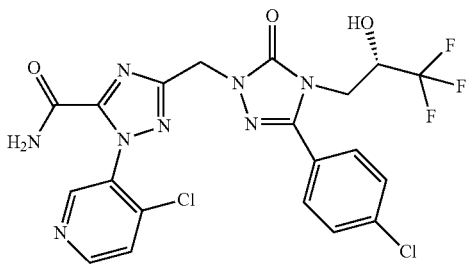 [SMILES: NC(=O)c1nc(Cn2nc(-c3ccc(Cl)cc3)n(C[C@H](O)C(F)(F)F)c2=O)nn1-c1cnccc1Cl]

100 mg Example 11A (0.179 mmol) was dissolved in 1.0 mL of an ammonia solution (7N in methanol, 7.09 mmol). The resulting mixture was stirred for 16 h at room temperature. The solvent was removed in vacuo and the crude product was purified by preparative HPLC (Method 5).

Lyophilisation of the product containing fractions afforded 76.7 mg (79% of th.) of the title compound as a solid.

LC-MS (Method 3): $R_t$=1.55 min; MS(ESIpos): m/z=543.1 [M+H]$^+$ $^1$H NMR (DMSO-d$_6$, 400 MHz): δ=8.91-7.52 (m, 9H), 6.90 (d, 1H), 5.17 (d, 2H), 4.40-4.18 (m, 1H), 4.07-3.72 (m, 2H).

Example 7

3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[4-(trifluoromethyl)pyridin-3-yl]-1H-1,2,4-triazole-5-carboxamide

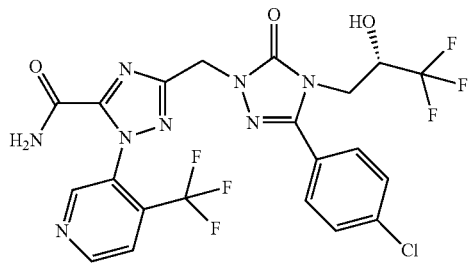 [SMILES: NC(=O)c1nc(Cn2nc(-c3ccc(Cl)cc3)n(C[C@H](O)C(F)(F)F)c2=O)nn1-c1cnccc1C(F)(F)F]

78.5 mg Example 12A (0.133 mmol) was dissolved in 8.0 mL of an ammonia solution (7N in methanol, 1.14 mmol). The resulting mixture was stirred for 1 h at room temperature. The solvent was removed in vacuo and the crude product was purified by preparative HPLC (Method 5). Lyophilisation of the product containing fractions afforded 49.7 mg (77% of th.) of the title compound as a solid.

LC-MS (Method 2): $R_t$=0.93 min; MS(ESIpos): m/z=577.1 [M+H]$^+$ $^1$H NMR (DMSO-d$_6$, 400 MHz): δ=9.03 (d, 1H), 8.97 (s, 1H), 8.36 (s, 1H), 8.00 (d, 2H), 7.86-7.70 (m, 2H), 7.69-7.58 (m, 2H), 6.90 (d, 1H), 5.17 (d, 2H), 4.39-4.20 (br m, 1H), 4.06-3.94 (m, 1H), 3.86 (dd, 1H).

Example 8

Ethyl 3-[5-carbamoyl-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]isonicotinate

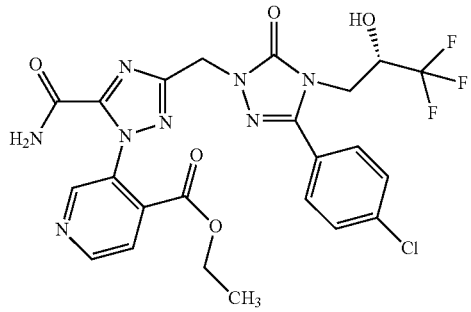 [SMILES: CCOC(=O)c1ccncc1-n1nc(Cn2nc(-c3ccc(Cl)cc3)n(C[C@H](O)C(F)(F)F)c2=O)nc1C(N)=O]

100 mg Example 13A (151 μmol) was dissolved in 1.0 mL NH$_3$ in EtOH (2.00 mmol, 2 N). The resulting mixture was stirred for 16 h at room temperature and another 1.0 mL of an ammonia solution (7N in methanol, 2.00 mmol) was added and stirring was continued for 16 h at room temperature. The solvent was removed in vacuo and the crude product was purified by preparative HPLC (Method 5). Lyophilisation of the product containing fractions afforded 46.0 mg (49% of th.) of the title compound as a solid.

LC-MS (Method 3): $R_t$=1.63 min; MS(ESIpos): m/z=581.1 [M+H]$^+$ $^1$H NMR (DMSO-d$_6$, 400 MHz): δ=8.89 (d, 1H), 8.83 (s, 1H), 8.28 (s, 1H), 7.94 (s, 1H), 7.90 (d, 1H), 7.78-7.72 (m, 2H), 7.69-7.58 (m, 2H), 6.89 (d, 1H), 5.14 (d, 2H), 4.40-4.24 (m, 1H), 4.10-3.96 (m, 3H), 3.86 (dd, 1H), 0.95 (t, 3H).

Example 9

2-[5-carbamoyl-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]nicotinamide

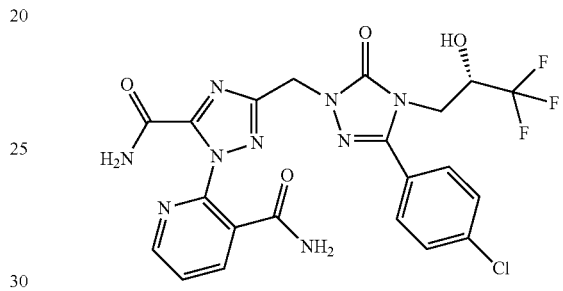

80 mg Example 10A (134 μmot) was dissolved in 10 mL of an ammonia solution (7N in methanol, 70.0 mmol). The resulting mixture was stirred for 10 min at 70° C., solvent was removed in vacuo and the residue was dissolved 10 mL of an ammonia solution (7N in methanol, 70.0 mmol) stirred for 3 h at 120° C. in the microwave. The solvent was removed in vacuo and the crude product was purified by preparative HPLC (Method 5). Lyophilisation of the product containing fractions afforded 22.0 mg (28% of th.) of the title compound as a solid.

LC-MS (Method 3): $R_t$=1.31 min; MS(ESIpos): m/z=552.1 [M+H]$^+$ $^1$H NMR (DMSO-d$_6$, 400 MHz): δ=8.61 (dd, 1H), 8.24-8.14 (m, 2H), 7.90-7.83 (m, 1H), 7.86 (br d, 1H), 7.79-7.74 (m, 2H), 7.69 (dd, 1H), 7.65-7.60 (m, 2H), 7.49 (s, 1H), 6.92 (d, 1H), 5.10 (d, 2H), 4.39-4.21 (br m, 1H), 4.06-3.93 (m, 1H), 3.84 (dd, 1H).

Example 10

3-({3-(4-Chlorophenyl)-5-oxo-4-[(2R)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide

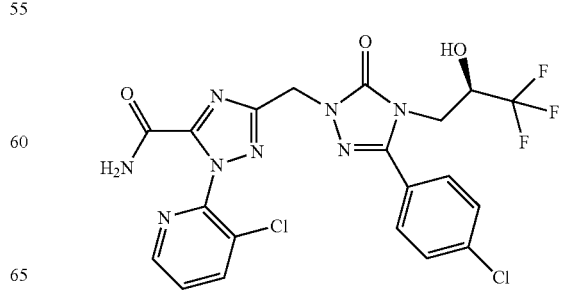

110 mg Example 14A (0.197 mmol) was dissolved in 1.0 mL of an ammonia solution (7N in methanol, 7.09 mmol). The resulting mixture was stirred for 1 h at room temperature. The solvent was removed in vacuo and the crude product was purified by preparative HPLC (Method 5). Lyophilisation of the product containing fractions afforded 92.0 mg (86% of th.) of the title compound as a solid.

LC-MS (Method 3): $R_t$=1.60 min; MS(ESIpos): m/z=543.1 [M+H]$^+$ $^1$H NMR (DMSO-d$_6$, 400 MHz): δ=8.69-7.48 (m, 9H), 6.90 (d, 1H), 5.18 (d, 2H), 4.47-4.16 (m, 1H), 4.08-3.71 (m, 2H).

Example 11

3-({3-(4-Chlorophenyl)-5-oxo-4-[(2R)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide

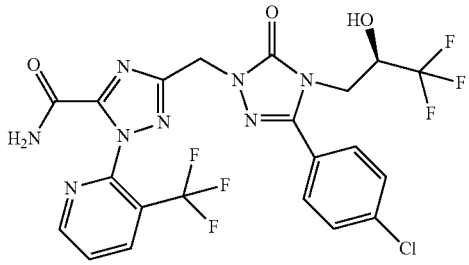 [SMILES: NC(=O)c1nc(Cn2nc(-c3ccc(Cl)cc3)n(C[C@@H](O)C(F)(F)F)c2=O)nn1-c1ncccc1C(F)(F)F]

160 mg Example 15A (270 μmol) was dissolved in 5.0 mL of an ammonia solution (7N in methanol, 2.00 mmol). The resulting mixture was stirred for 1.5 h at room temperature. The solvent was removed in vacuo and the crude product was purified by preparative HPLC (Method 5). Lyophilisation of the product containing fractions afforded 162.1 mg (quant.) of the title compound as a solid.

LC-MS (Method 4): $R_t$=2.73 min; MS(ESIpos): m/z=577.3 [M+H]$^+$ $^1$H NMR (DMSO-d$_6$, 400 MHz): δ=8.90-8.81 (m, 1H), 8.51 (dd, 1H), 8.39 (s, 1H), 7.99 (s, 1H), 7.90 (dd, 1H), 7.80-7.70 (m, 2H), 7.66-7.59 (m, 2H), 6.90 (d, 1H), 5.25-5.12 (m, 2H), 4.40-4.20 (br m, 1H), 4.03-3.96 (m, 1H), 3.85 (dd, 1H).

Example 12

3-({3-(4-Chlorophenyl)-5-oxo-4-[(2R)-3,3,3-trifluoro-2-hydroxypropyl]-4,5-dihydro-1H-1,2,4-triazol-1-yl}methyl)-1-(4-chloropyridin-3-yl)-1H-1,2,4-triazole-5-carboxamide

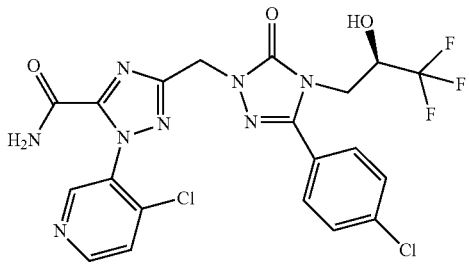 [SMILES: NC(=O)c1nc(Cn2nc(-c3ccc(Cl)cc3)n(C[C@@H](O)C(F)(F)F)c2=O)nn1-c1cnccc1Cl]

118 mg Example 16A (211 μmol) was dissolved in 5.0 mL of an ammonia solution (7N in methanol, 35.0 mmol). The resulting mixture was stirred for 1 h at room temperature. The solvent was removed in vacuo and the crude product was purified by preparative HPLC (Method 5). Lyophilisation of the product containing fractions afforded 111 mg (97% of th.) of the title compound as a solid.

LC-MS (Method 3): $R_t$=1.53 min; MS(ESIpos): m/z=543.1 [M+H]$^+$ $^1$H NMR (DMSO-d$_6$, 400 MHz): δ=8.78 (s, 1H), 8.69 (d, 1H), 8.35 (s, 1H), 8.01 (s, 1H), 7.82 (d, 1H), 7.79-7.73 (m, 2H), 7.66-7.58 (m, 2H), 6.90 (d, 1H), 5.17 (d, 2H), 4.39-4.20 (br m, 1H), 4.07-3.95 (m, 1H), 3.85 (dd, 1H).

Example 13

3-({3-(4-Chlorophenyl)-5-oxo-4-[(2R)-3,3,3-trifluoro-2-hydroxypropyl]-4,5-dihydro-1H-1,2,4-triazol-1-yl}methyl)-1-[4-(trifluoromethyl)pyridin-3-yl]-1H-1,2,4-triazole-5-carboxamide

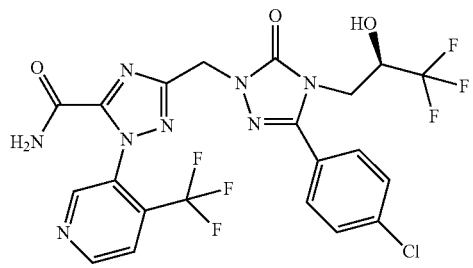 [SMILES: NC(=O)c1nc(Cn2nc(-c3ccc(Cl)cc3)n(C[C@@H](O)C(F)(F)F)c2=O)nn1-c1cnccc1C(F)(F)F]

118 mg Example 17A (199 μmol) was dissolved in 5.0 mL of an ammonia solution (7N in methanol, 2.00 mmol). The resulting mixture was stirred for 20 min at room temperature. The solvent was removed in vacuo and the crude product was purified by preparative HPLC (Method 5). Lyophilisation of the product containing fractions afforded 99.5 mg (87% of th.) of the title compound as a solid.

LC-MS (Method 3): $R_t$=1.63 min; MS(ESIpos): m/z=577.1 [M+H]$^+$ $^1$H NMR (DMSO-d$_6$, 400 MHz): δ=9.03 (d, 1H), 8.96 (s, 1H), 8.36 (s, 1H), 8.00 (d, 2H), 7.77-7.70 (m, 2H), 7.68-7.59 (m, 2H), 6.89 (d, 1H), 5.28-5.05 (m, 2H), 4.39-4.20 (br m, 1H), 4.05-3.96 (m, 1H), 3.85 (dd, 1H).

Example 14

3-{[3-(4-Chlorophenyl)-5-oxo-4-(3,3,3-trifluoro-2-oxopropyl)-4,5-dihydro-1H-1,2,4-triazol-1-yl]methyl}-1-(3-chloropyridin-2-yl)-1H-1,2,4-triazole-5-carboxamide (ketone form) or 3-{[3-(4-chlorophenyl)-5-oxo-4-(3,3,3-trifluoro-2,2-dihydroxypropyl)-4,5-dihydro-1H-1,2,4-triazol-1-yl]methyl}-1-[2-(trifluoromethyl)phenyl]-1H-1,2,4-triazole-5-carboxamide (hydrate form)

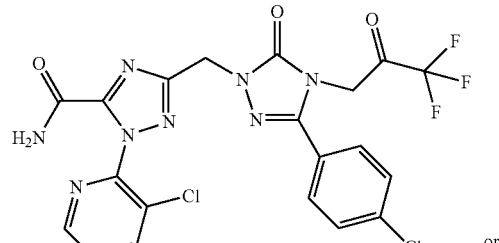

or

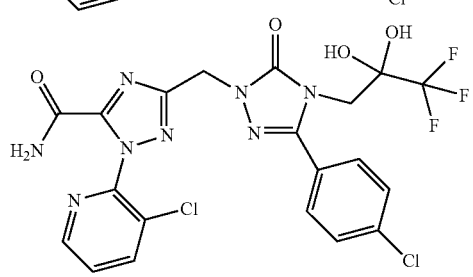

A solution of 250 mg of example 1 (460 μmol) in 5.0 ml dichloromethane was cooled to 0° C. and 780 mg (1.84 mmol) of Dess-Martin periodinane and 9.0 μL (506 mmol) water were added. The resulting mixture was stirred for 1 h. at room temperature. To the reaction mixture 5 mL of saturated aqueous sodium thiosulfate solution and 5 mL of saturated aqueous sodium bicarbonate solution were added and the resulting mixture was stirred for 10 min. The phases were separated and the aqueous layer was extracted with ethyl acetate (10 mL, three times repeated), the combined organic phases were dried over magnesium sulfate and evaporated. The crude product was purified by preparative HPLC (Method 5). Lyophilisation of the product containing fractions afforded 230 mg (87% of th.) of the title compound as a solid LC-MS (Method 3): $R_t$=1.57 min; MS(ESIpos): m/z=541.0 [M+H]$^+$ (ketone form).

$^1$H NMR (DMSO-$d_6$, 400 MHz): δ=8.54 (dd, 1H), 8.40 (s, 1H), 8.25 (dd, 1H), 8.00 (s, 1H), 7.76-7.63 (m, 3H), 7.62-7.53 (m, 2H), 7.44 (s, 2H), 5.19 (s, 2H), 4.05 (s, 2H)) (hydrate form).

Example 15

1-(3-Bromopyridin-2-yl)-3-{[3-(4-chlorophenyl)-5-oxo-4-(3,3,3-trifluoro-2-oxopropyl)-4,5-dihydro-1H-1,2,4-triazol-1-yl]methyl}-1H-1,2,4-triazole-5-carboxamide (ketone form) or 1-(3-Bromopyridin-2-yl)-3-{[3-(4-chlorophenyl)-5-oxo-4-(3,3,3-trifluoro-2,2-dihydroxypropyl)-4,5-dihydro-1H-1,2,4-triazol-1-yl]methyl}-1H-1,2,4-triazole-5-carboxamide (hydrate form)

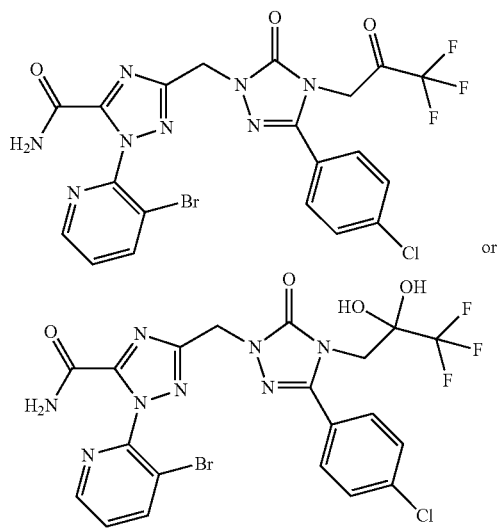

A solution of 68.0 mg of example 4 (116 μmol) in 1.3 ml dichloromethane was cooled to 0° C. and 196 mg (463 mmol) of Dess-Martin periodinane and 2.3 μL (127 mmol) water were added. The resulting mixture was warmed to room temperature and then stirred for 1 h. To the reaction mixture 1.3 mL of saturated aqueous sodium thiosulfate solution and 1.3 mL of saturated aqueous sodium bicarbonate solution were added and the mixture was stirred for 10 min. The phases were separated and the aqueous layer was extracted with ethyl acetate (3×10 mL), the combined organic phases were then dried over magnesium sulfate and evaporated. The crude product was purified by preparative HPLC (Method 5). Lyophilisation of the product containing fractions afforded 30.1 mg (42% of th.) of the title compound as a solid LC-MS (Method 3): $R_t$=1.58 min; MS(ESIpos): m/z=585.0 [M+H]$^+$ (ketone form).

$^1$H NMR (DMSO-$d_6$, 400 MHz): δ=8.57 (dd, 1H), 8.40-8.34 (m, 2H), 7.98 (s, 1H), 7.72 (s, 1H), 7.70 (s, 1H), 7.58 (d, 3H), 7.44 (s, 2H), 5.20-5.16 (m, 2H), 4.05 (s, 2H) (hydrate form).

Example 16

3-{[3-(4-Chlorophenyl)-5-oxo-4-(3,3,3-trifluoro-2-oxopropyl)-4,5-dihydro-1H-1,2,4-triazol-1-yl]methyl}-1-(4-chloropyridin-3-yl)-1H-1,2,4-triazole-5-carboxamide (ketone form) or 3-{[3-(4-Chlorophenyl)-5-oxo-4-(3,3,3-trifluoro-2,2-dihydroxypropyl)-4,5-dihydro-1H-1,2,4-triazol-1-yl]-methyl}-1-(4-chloropyridin-3-yl)-1H-1,2,4-triazole-5-carboxamide (hydrate form)

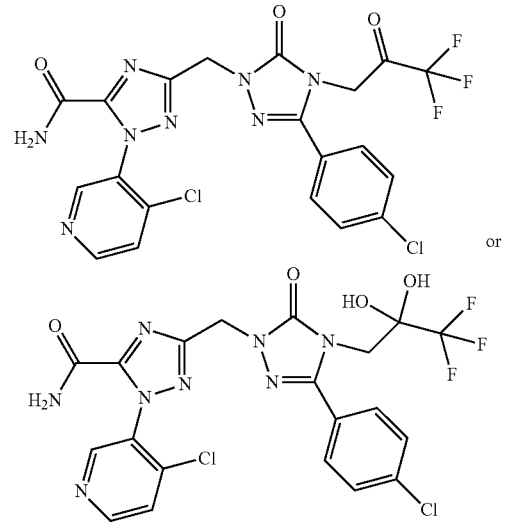

A solution of 120 mg of example 6 (221 μmol) and 4.3 μL, (243 mmol) water in 2.4 ml dichloromethane was cooled to 0° C. and 140.5 mg (331 mmol) Dess-Martin periodinane were then added. The resulting mixture was warmed to room temperature and then stirred for 2 h. To the suspension 5 mL THF was added and stirring was prolonged for 72 h at 4° C. followed by further 3 h at room temperature. To the reaction mixture 2 mL saturated aqueous sodium thiosulfate solution and 2 mL saturated aqueous sodium bicarbonate solution were added and the mixture was then stirred for 10 min. The phases were separated and the aqueous layer was extracted with dichloromethane (10 mL, four times repeated), the combined organic phases were washed with water and aqueous saturated sodium chloride solution, dried over magnesium sulfate and evaporated. The crude product was purified by flash chromatography (silica gel, cyclohexane/ethyl acetate 1:1→ethyl acetate). Evaporating of the product containing fractions afforded 8.0 mg (7% of th.) of the title compound as a solid LC-MS (Method 4): $R_t$=2.43 min; MS(ESIpos): m/z=541.2 [M+H]$^+$ (ketone form).

$^1$H NMR (DMSO-$d_6$, 400 MHz): δ=8.78 (s, 1H), 8.69 (d, 1H), 8.36 (s, 1H), 8.00 (s, 1H), 7.82 (d, 1H), 7.71 (d, 2H), 7.58 (d, 2H), 7.43 (s, 2H), 5.19 (s, 2H), 4.06 (s, 2H) (hydrate form).

Example 17

3-{[3-(4-Chlorophenyl)-5-oxo-4-(3,3,3-trifluoro-2-oxopropyl)-4,5-dihydro-1H-1,2,4-triazol-1-yl]methyl}-1-[3-(trifluoromethyl)pyridin-2-yl]-1H-1,2,4-triazole-5-carboxamide (ketone form) or 3-{[3-(4-Chlorophenyl)-5-oxo-4-(3,3,3-trifluoro-2,2-dihydroxypropyl)-4,5-dihydro-1H-1,2,4-triazol-1-yl]methyl}-1-[3-(trifluoromethyl)pyridin-2-yl]-1H-1,2,4-triazole-5-carboxamide (hydrate form)

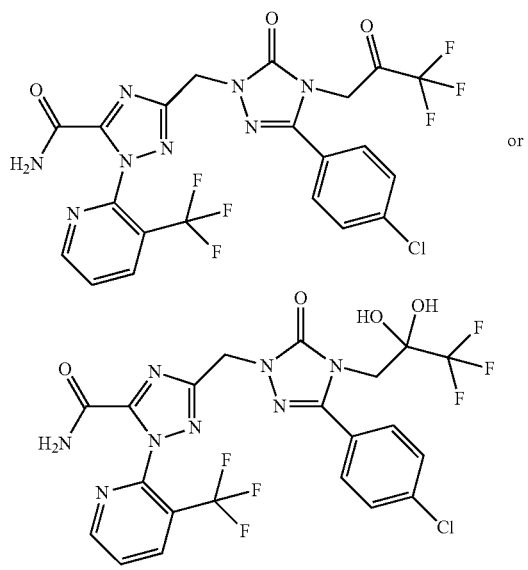

A solution of 100 mg of example 2 (173 µmol) in 1.9 ml dichloromethane was cooled to 0° C. and 294 mg (693 mmol) Dess-Martin periodinane and 3.5 µL, (191 mmol) water were then added. The resulting mixture was warmed to room temperature and then stirred for 1 h. To the reaction mixture 2 mL saturated aqueous sodium thiosulfate solution and 2 mL saturated aqueous sodium bicarbonate solution were added and the resulting mixture then stirred for 10 min. The aqueous layer was extracted with dichloromethane (10 mL, four times repeated), the combined organic phases were washed with water and aqueous saturated sodium chloride solution, dried over magnesium sulfate and evaporated. The crude product was purified by preparative HPLC (Method 5). Lyophilisation of the product containing fractions afforded 18.4 mg (19% of th.) of the title compound as a solid LC-MS (Method 3): $R_t$=1.64 min; MS(ESIpos): m/z=575.0 [M+H]$^+$ (ketone form).

$^1$H NMR (DMSO-d$_6$, 400 MHz): δ=8.88-8.85 (m, 1H), 8.51 (dd, 1H), 8.40 (s, 1H), 7.98 (s, 1H), 7.90 (dd, 1H), 7.73-7.67 (m, 2H), 7.58 (d, 2H), 7.43 (s, 2H), 5.18 (s, 2H), 4.05 (s, 2H) (hydrate form).

EXPERIMENTAL SECTION

Biological Assays

Abbreviations and Acronyms
Acc. No. accession number
AVP arginine vasopressin
$B_{max}$ maximal ligand binding capacity
BSA bovine serum albumin
cAMP cyclic adenosine monophosphate
Cat. No. catalogue number
cDNA complementary deoxyribonucleic acid
CHO chinese hamster ovary
CRE cAMP response element
Ct cycle threshold
DMEM/F12 Dulbecco's modified Eagle's medium/Ham's F12 medium (1:1)
DNA deoxyribonucleic acid
DMSO dimethylsulfoxide
DTT dithiothreitol
$EC_{50}$ half-maximal effective concentration
EDTA ethylenediamine-tetraacetic acid
FAM carboxyfluorescein succinimidyl ester
f.c. final concentration
FCS fetal calf serum
HEPES 4-(2-hydroxyethyl)piperazine-1-ethanesulfonic acid
$IC_{50}$ half-maximal inhibitory concentration
$K_d$ dissociation constant
$K_i$ dissociation constant of an inhibitor
mRNA messenger ribonucleic acid
PBS phosphate buffered saline
PEG polyethylene glycol
p.o. per os, peroral
RNA ribonucleic acid
RTPCR real-time polymerase chain reaction
SPA scintillation proximity assay
TAMRA carboxytetramethylrhodamine
TRIS; Tris 2-amino-2-hydroxymethylpropane-1,3-diol Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Demonstration of the activity of the compounds of the present invention may be accomplished through in vitro, ex vivo, and in vivo assays that are well known in the art. For example, to demonstrate the activity of the compounds of the present invention, the following assays may be used.

B-1. Cellular In Vitro Assay for Determining Vasopressin Receptor Activity

The identification of agonists and antagonists of the V1a and V2 vasopressin receptors from humans, rats and dogs as well as the quantification of the activity of the compounds of the invention is carried out using recombinant cell lines. These cell lines originally derive from a hamster's ovary epithelial cell (Chinese Hamster Ovary, CHO K1, ATCC: American Type Culture Collection, Manassas, Va. 20108, USA). The test cell lines constitutively express the human, rat or dog V1a or V2 receptors. In case of the $G_{\alpha_q}$-coupled V1a receptors, cells are also stably transfected with a modified form of the calcium-sensitive photoproteins aequorin (human and rat V1a) or obelin (dog V1a), which, after reconstitution with the cofactor coelenterazine, emit light when there are increases in free calcium concentrations [Rizzuto R, Simpson A W, Brini M, Pozzan T, Nature 358, 325-327 (1992); Illarionov B A, Bondar V S, Illarionova V A, Vysotski E S, *Gene* 153 (2), 273-274 (1995)]. The resulting vasopressin receptor cells react to stimulation of the recombinantly expressed V1a receptors by intracellular release of calcium ions, which can be quantified by the resulting photoprotein luminescence. The $G_s$-coupled V2 receptors are stably transfected into cell lines expressing the gene for firefly luciferase under control of a CRE-responsible promoter. Activation of V2 receptors induces the activation of the CRE-responsive promoter via cAMP increase, thereby inducing the expression of firefly luciferase. The light emitted by photoproteins of V1a cell lines as well as the light emitted by firefly luciferase of V2 cell lines corresponds to the activation or inhibition of the respective vasopressin receptor. The bioluminescence of the cell lines is detected using a suitable luminometer [Milligan G, Marshall F, Rees S, *Trends in Pharmacological Sciences* 17, 235-237 (1996)].

Test Procedure:

Vasopressin V1a Receptor Cell Lines:

On the day before the assay, the cells are plated out in culture medium (DMEM/F12, 2% FCS, 2 mM glutamine, 10 mM HEPES, 5 μg/ml coelenterazine) in 384-well microtiter plates and kept in a cell incubator (96% humidity, 5% v/v $CO_2$, 37° C.). On the day of the assay, test compounds in various concentrations are placed for 10 minutes in the wells of the microtiter plate before the agonist [$Arg^8$]-vasopressin at $EC_{50}$ concentration is added. The resulting light signal is measured immediately in a luminometer.

Vasopressin V2 Receptor Cell Lines:

On the day before the assay, the cells are plated out in culture medium (DMEM/F12, 2% FCS, 2 mM glutamine, 10 mM HEPES) in 384-well microtiter plates and kept in a cell incubator (96% humidity, 5% v/v $CO_2$, 37° C.). On the day of the assay, test compounds in various concentrations and the agonist [$Arg^8$]-vasopressin at $EC_{50}$ concentration are added together to the wells, and plates are incubated for 3 hours in a cell incubator. Upon addition of the cell lysis reagent Triton™ and the substrate luciferin, luminescence of firefly luciferase is measured in a luminometer.

Table 1A below lists individual $IC_{50}$ values for the compounds of the invention (including racemic mixtures as well as separated enantiomers) that were obtained from cell lines transfected with the human V1a or V2 receptor:

TABLE 1A

| Example No. | $IC_{50}$ hV1a [μM] | $IC_{50}$ hV2 [μM] | ratio $IC_{50}$ hV2/hV1a |
|---|---|---|---|
| 1 | 0.00102 | 0.03900 | 38.2 |
| 2 | 0.00120 | 0.16966 | 141.0 |
| 3 | 0.01600 | 0.87500 | 54.7 |
| 4 | 0.00123 | 0.08933 | 72.6 |
| 5 | 0.01450 | 1.24500 | 85.9 |
| 6 | 0.00057 | 0.02500 | 43.9 |
| 7 | 0.00250 | 0.29333 | 117.3 |
| 8 | 0.02550 | 0.89250 | 35.0 |
| 9 | 0.07500 | 2.25000 | 30.0 |
| 10 | 0.00680 | 0.79000 | 116.2 |
| 11 | 0.00310 | 0.61000 | 196.8 |
| 12 | 0.00345 | 0.86000 | 249.3 |
| 13 | 0.00160 | 0.69000 | 431.3 |
| 14 | 0.00520 | 0.10375 | 20.0 |
| 15 | 0.01350 | 0.63667 | 47.2 |
| 16 | 0.00140 | 0.07500 | 53.6 |
| 17 | 0.00530 | 0.35000 | 66.0 |

The $IC_{50}$ data listed in Table 1A demonstrate that the compounds of the present invention are acting as selective and potent vasopressin V1a receptor antagonists.

For comparative purposes, selected phenyl-triazole derivatives that were regarded to be representative of closest prior art (cf. Int. Pat. Appl. WO 2011/104322-A1 and example compounds described therein) were also tested in the cellular V1a and V2 assays described above. $IC_{50}$ values for these compounds obtained from cell lines transfected with the human V1a or V2 receptor are listed in Table 1B below:

TABLE 1B

| Example No. WO 2011/104322 | $IC_{50}$ hV1a [μM] | $IC_{50}$ hV2 [μM] | ratio $IC_{50}$ hV2/hV1a |
|---|---|---|---|
| 54 | 0.0114 | 0.0402 | 3.51 |
| 63 | 0.0068 | 0.0042 | 0.622 |
| 64 | 0.0329 | 0.0345 | 1.049 |
| 66 | 1.8265 | 0.0950 | 0.052 |
| 67 | 2.4650 | 1.1400 | 0.462 |
| 68 | 0.0071 | 0.0096 | 1.353 |
| 69 | 1.3160 | 0.0699 | 0.053 |
| 101 | 0.0678 | 0.0342 | 0.503 |
| 105 | 0.3238 | 0.0551 | 0.170 |
| 135 | 0.2500 | 0.0098 | 0.04 |
| 143 | 0.4590 | 0.9090 | 1.98 |
| 144 | 0.2800 | 0.2410 | 0.86 |
| 148 | 2.2200 | 0.0707 | 0.03 |

For comparative purposes, further selected phenyl-triazole derivatives that were regarded to be representative of closest prior art (cf. Int. Pat. Appl. WO 2016/071212-A1 and example compounds described therein) were also tested in the cellular V1a and V2 assays described above. $IC_{50}$ values for these compounds obtained from cell lines transfected with the human V1a or V2 receptor are listed in Table 1C below:

TABLE 1C

| Example No. WO 2016/071212 | $IC_{50}$ hV1a [μM] | $IC_{50}$ hV2 [μM] | ratio $IC_{50}$ hV2/hV1a |
|---|---|---|---|
| 4 | 0.0012 | 0.0086 | 6.94 |
| 8 | 0.0012 | 0.0107 | 8.78 |
| 73 | 0.0011 | 0.0070 | 6.48 |
| 74 | 0.0022 | 0.0247 | 11.44 |
| 82 | 0.0006 | 0.0022 | 3.43 |
| 83 | 0.0010 | 0.0067 | 6.48 |

B-2. Radioactive Binding Assay $IC_{50}$ and $K_i$ values can be determined in radioactive binding assays using membrane fractions of recombinant human embryonic kidney cell line 293 (HEK293) or CHO-K1 cell lines expressing the respective human vasopressin V1a and V2 receptors.

Human recombinant vasopressin V1a receptors expressed in HEK293 cells are used in 50 mM Tris-HCl buffer, pH 7.4, 5 mM $MgCl_2$, 0.1% BSA using standard techniques. Aliquots of prepared membranes are incubated with test compounds in various concentrations in duplicates and 0.03 nM [$^{125}$I]Phenylacetyl-D-Tyr(Me)-Phe-Gln-Asn-Arg-Pro-Arg-Tyr-$NH_2$ for 120 minutes at 25° C. Nonspecific binding is estimated in the presence of 1 μM [$Arg^8$]Vasopressin. Receptors are filtered and washed, the filters are then counted to determine [$^{125}$I]Phenylacetyl-D-Tyr(Me)-Phe-Gln-Asn-Arg-Pro-Arg-Tyr-$NH_2$ specifically bound.

CHO-K1 cells stably transfected with a plasmid encoding human vasopressin V2 receptor are used to prepare membranes in 50 mM Tris-HCl buffer, pH 7.4, 10 mM $MgCl_2$, 0.1% BSA using standard techniques. Aliquots of prepared membrane are incubated with test compounds in various concentrations in duplicates and 4 nM [$^3$H]($Arg^8$)-Vasopressin for 120 minutes at 25° C. Nonspecific binding is estimated in the presence of 1 mM ($Arg^8$)-vasopressin. Membranes are filtered and washed 3 times and the filters are counted to determine [$^3$H]($Arg_8$)-Vasopressin specifically bound.

$IC_{50}$ values are determined by a non-linear, least squares regression analysis using MathIQ™ (ID Business Solutions Ltd., UK). The inhibition constant $K_i$ is calculated using the equation of Cheng and Prusoff (Cheng, Y., Prusoff, W. H., Biochem. Pharmacol. 22:3099-3108, 1973).

B-3. Cellular In Vitro Assay for Detecting the Action of Vasopressin V1a Receptor Antagonists on the Regulation of Pro-Fibrotic Genes The cell line $H9C_2$ (American Type Culture Collection ATCC No. CRL-1446), described as a cardiomyocyte type isolated from rat cardiac tissue, endogenously expresses the vasopressin V1a receptor AVPR1A in high copy number, whereas AVPR2 expression cannot be detected. Likewise, the cell line NRK49F (ATCC No. CRL1570) isolated from rat kidney tissue, shows similar expression pattern of high AVPR1A mRNA expression and diminishing AVPR2 expression. For cell assays detecting the inhibition of AVPR1A receptor-dependent regulation of gene expression by receptor antagonists, the procedure is as follows:

$H9C_2$ cells or NRK49F cells are seeded in 6-well microtiter plates for cell culture at a cell density of 50 000 cells/well in 2.0 ml of Opti-MEM medium (Invitrogen Corp., Carlsbad, Calif., USA, Cat. No. 11058-021) and held in a cell incubator (96% humidity, 8% v/v $CO_2$, 37° C.). After 24 hours, sets of three wells (triplicate) are charged with vehicle solution (negative control) and vasopressin solution ([Arg8]-vasopressin acetate, Sigma, Cat. No. V9879), or test compound (dissolved in vehicle: water with 20% v/v ethanol) and vasopressin solution. In the cell culture, the final vasopressin concentration is 1 nM. The test compound solution is added to the cell culture in small volumes, so that a final concentration of 0.03% of ethanol in the cell assay is not exceeded. After an incubation time of 5 hours, the culture supernatant is drawn off under suction, the adherent cells are lysed in 350 μl of RLT buffer (Qiagen, Cat. No. 79216), and the RNA is isolated from the lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and Reverse Transcription Polymerase Chain Reaction (RTPCR) (pPCR MasterMix RT-QP2X-03-075, Eurogentec, Seraing, Belgium). All procedures take place in accordance with the working protocols of the test reagents' manufacturers. The primer sets for the RTPCR are selected on the basis of the mRNA gene sequences (NCBI GenBank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 384-well microtiter plate format in accordance with the instrument operating instructions. The relative gene expression is represented by the delta-delta Ct value [Applied Biosystems, User Bulletin No. 2 ABI Prism 7700 SDS, Dec. 11, 1997 (updated October 2001)] with reference to the level of expression of the ribosomal protein L-32 gene (GenBank Acc. No. NM_013226) and the threshold Ct value of Ct=35.

B-4. Inhibition of Vasopressin Induced Aggregation of Human Platelets

Human platelets endogenously express the V1a receptor. It was found that relatively high vasopressin concentrations (ca. 50-100 nM) stimulate platelet aggregation ex vivo. Therefore, platelets enriched from human blood may serve as a V1a expressing tissue for pharmacological studies with corresponding high concentrations of vasopressin antagonists.

Human blood is collected in a 10 mM trisodium citrate solution by venous puncture from nonsmoking healthy volunteers (n=4-8) who were drug free for at least 1 week. Platelet-rich plasma (PRP) is obtained by centrifuging the blood sample at 140 g for 20 min at 4° C. The resulting pellet is further centrifuged (15.000 rpm, 2 min) to produce platelet-poor plasma (PPP). Platelet aggregation is measured turbidimetrically using an aggregometer (APACT 4). The reaction is followed by monitoring changes in light transmission on 178 μL PRP aliquots, under continuous stirring at 37° C., against PPP control. Various concentrations of vasopressin antagonists (in 2 μL) are added to PRP 5 min before the addition of 20 μL Arg-vasopressin (final concentration 100 nM. The inhibitory effects of the compounds are determined by measuring the height of the aggregation wave from the bottom of the shape change compared with the control response. $IC_{50}$ values are calculated a dose-response inhibition curve by an iterative nonlinear regression program B-5. Effects on the Contraction of Isolated Rat Vessel Rings Isolated Aorta Test compounds can be investigated on isolated aortic rings from male Wistar rats endogenously expressing the Via receptor. Male Wistar rats are euthanized using carbon dioxide. The aorta is removed and placed in ice-cold Krebs-Henseleit buffer of following composition (in mmol/1): NaCl 112, KCl 5.9, $CaCl_2$ 2.0, $MgCl_2$ 1.2, $NaH_2PO_4$ 1.2, $NaHCO_3$ 25, glucose 11.5. The aorta is cut into 3 mm rings and transferred to 20 ml organ baths containing Krebs-Henseleit solution equilibrated with 95% $O_2$, 5% $CO_2$ at 37° C. For recording of isometric tension the rings are mounted between two hooks. The resting tension is adjusted to 3 g. After an equilibration period, each experiment is started by exposing the preparation to K+(50 mM) Krebs-Henseleit solution. The aortic rings are than pre-contracted using 1 nmol/1 Arg-vasopressin. After a stable contraction is established, a cumulative dose response curve of the test compound is constructed. The stabilized contraction induced by Arg-vasopressin is defined as 100% tension. The relaxation is expressed as percentage tension.

Isolated *A. renalis*

Male Wistar rats (200-250 g) are euthanized using carbon dioxide. The *A. renalis* is removed and placed in ice-cold Krebs-Henseleit buffer of following composition (in mmol/1): NaCl 112, KCl 5.9, $CaCl_2$ 2.0, $MgCl_2$ 1.2, $NaH_2PO_4$ 1.2, $NaHCO_3$ 25, glucose 11.5. For measurement of isometric tension, ring segments, 2 mm in length, are mounted in a small vessel chamber myograph (Danish Myo Technology A/S, Denmark) using two tungsten wires fixed to mounting jaws. One mounting jaw is attached to a micrometer, allowing control of vessel circumference. The other mounting jaw is attached to a force transducer for measurement of tension development. The whole preparation is kept in a chamber with physiological salt solution at 37° C., bubbled with oxygen. After a 30 min equilibration period, the vessels are stretched to their optimal lumen diameter for active tension development which is determined based on the internal circumference-wall tension ratio. The internal circumference is set to 90% of what the vessels would have if they are exposed to a passive tension equivalent to that produced by a transmural pressure of 100 mmHg Afterwards, the vessels are washed three times with Krebs-Henseleit buffer and left to equilibrate for 30 mM. The contractility is then tested by a twofold exposure to a high $K^+$ solution (50 mmol/l KCl). After washing with Krebs-Henseleit buffer the vessels are then pre-contracted using 1 nmol/1 Arg-vasopressin. After a stable contraction is established, a cumulative dose response curve of the test compound is constructed. The stabilized contraction induced by Arg-vasopressin is defined as 100% tension. The relaxation is expressed as percentage tension.

B-6. In Vivo Assay for Detecting Cardiovascular Effects: Blood Pressure Measurement in Anaesthetized Rats (Vasopressin 'Challenge' Model)

Male Sprague-Dawley rats (250-350 g body weight) are used under ketamine/xylazine/pentobarbital injection anaesthesia. Polyethylene tubes (PE-50, Intramedic®), prefilled with heparin-containing (500 IU/ml) isotonic sodium chloride solution, are introduced into the jugular vein and the femoral vein and then tied in. Arg-vasopressin (SIGMA) is injected via one venous access, with the aid of a syringe; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment, the experimental animal is administered 3-4 successive bolus injections at intervals of 10-15 min with a defined amount of Arg-vasopressin (30 ng/kg) in isotonic sodium chloride solution. When the blood pressure has reached initial levels again, the test substance is administered as a bolus, with subsequent continuous infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of Arg-vasopressin. Control animals only receive solvent instead of the test substance.

Following intravenous administration, the compounds of the invention, in comparison to the solvent controls, bring about an inhibition of the blood pressure increase caused by Arg-vasopressin.

B-7. In Vivo Assay for Detecting Protective Renal Effects: Acute Ischemia/Reperfusion Injury Model in Rodents Laboratory bred male C57Bl/6J mice 6-8 weeks old are obtained from Taconic Biosciences, male 6-8 weeks old Sprague Dawley® rat are obtained from Charles River. Both rats and mice are maintained under standard laboratory conditions, 12 hour light-dark cycles with access to normal chow and drinking water at libitum. For the ischemia reperfusion injury model a total of 10-12 rats or mice is used in each control and experimental group.

Animals are anesthetized with continuous inhaled isoflurane. A right nephrectomy is performed through a right flank incision 7 days before the ischemic procedures in the contralateral kidneys. For renal ischemia a left flank incision is made. Renal vessels are exposed by dissection of the left renal pedicle. Non-traumatic vascular clamps are used to stop blood flow (artery and vein) during 45 min (rats) or 25 min (mice) of ischemia. Reperfusion is established by removing the clamps. The abdominal wall (muscular layer and skin) is closed with 5.0 polypropylene sutures. Temgesic® (Buprenorphin, 0.025 mg/kg s.c.) is applied as an analgesic.

Urine of each animal is collected in metabolic cages over night before sacrifice at 24 h post ischemia. Upon sacrifice, blood samples are obtained under terminal anesthesia. After centrifugation of the blood samples, serum is isolated. Both serum creatinine and serum urea are measured via clinical biochemistry analyzer (Pentra 400). For the assessment of serum and urinary kidney injury biomarkers (Neutrophil gelatinase-associated lipocalin [NGAL], kidney injury molecule-1 [KIM-1] and Osteopontin) ELISA's are performed according to the manufacturers protocol. Both urinary creatinine and albumin are measured to determine the albumin/creatinine ratio.

Total RNA is isolated from kidneys. Left kidneys are snap-frozen in liquid nitrogen at sacrifice. Kidney tissue is then homogenized and RNA is obtained. Total RNA is transcribed to cDNA. Using TaqMan real-time PCR renal NGAL, Osteopontin, KIM-1, Nephrin and Podocin mRNA expression is analyzed in whole kidney tissue.

Differences between groups are analyzed by one-way ANOVA with Dunnett's corrections for multiple comparisons. Statistical significance is defined as $p<0.05$. All statistical analyses are done using GraphPad Prism 6.

B-8. In Vivo Assay for Detecting Cardiovascular Effects: Hemodynamic Investigations in Anaesthetized Dogs Male beagle dogs (Beagle, Marshall BioResources, USA) with a weight of between 10 and 15 kg are anesthetized with pentobarbital (30 mg/kg iv, Narcoren®, Merial, Germany) for the surgical interventions and the hemodynamic and functional investigation termini. Pancuroniumbromide (Pancuronium Inresa, Inresa, Germany, 2-4 mg/animal i.v.) serves additionally as a muscle relaxant. The dogs are intubated and ventilated with an oxygen/ambient air mixture (30/70%), about 2,5-4 L/min. Ventilation takes place using a ventilator from GE Healthcare (Avance, Germany) and is monitored using a carbon dioxide analyzer (-Datex Ohmeda). The anesthesia is maintained by continual infusion of pentobarbital (50 µg/kg/min); fentanyl is used as an analgesic (10 µg/kg/h).

In preparatory interventions, the dogs are fitted with a cardiac pacemaker. At start of experiment, a cardiac pacemaker from Biotronik (Logos®, Germany) is implanted into a subcutaneous skin pocket and is contacted with the heart via a pacemaker electrode (Siello S60®, Biotronik, Germany) which is advanced through the external jugular vein, with illumination, into the right ventricle.

Thereafter accesses are removed and the dog wakes spontaneously from the anesthesia. After a further 7 days, the above-described pacemaker is activated and the heart is stimulated at a frequency of 220 beats per minute.

The actual drug testing experiments take place 28 days after the beginning of pacemaker stimulation, using the following instrumentation:

Introduction of a bladder catheter for bladder relief and for measuring the flow of urine Attachment of electrocardiography (ECG) leads to the extremities for ECG measurement Introduction of a sheath introducer filled with sodium chloride solution into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through a port secured in the carotid artery, for measuring cardiac hemodynamics.

Introduction of a Swan-Ganz catheter (CCOmbo 7.5 F, Edwards, Irvine, USA) via the jugular vein into the pulmonary artery, for measuring the cardiac output, oxygen saturation, pulmonary arterial pressures and central venous pressure Siting of a venous catheter in the cephalic vein, for infusing pentobarbital, for liquid replacement and for blood sampling (determination of the plasma levels of substance or other clinical blood values)

Siting of a venous catheter in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (ACQ7700, Data Sciences International, USA or Edwards-Vigilance-Monitor, Edwards, Irvine, USA) and subsequently fed into the Ponemah system (Data Sciences International, USA) for evaluation. The signals are recorded continuously throughout the experimental period, and are further processed digitally by said software, and averaged over 30 seconds.

B-9. Determination of Pharmacokinetic Parameters Following Intravenous and Oral Administration The pharmacokinetic parameters of the compounds according to the invention are determined in male C57bl6-mice, male Wistar rats, female Beagle dogs and female Cynomolgus monkeys. Intravenous administration in the case of mice and rats is carried out by means of a species-specific plasma/DMSO formulation, and in the case of dogs and monkeys by means of a water/PEG400/ethanol formulation. In all species, oral administration of the dissolved substance is performed via gavage, based on a water/PEG400/ethanol formulation. The taking of blood from rats is simplified by inserting a silicone catheter into the right Vena jugularis externa prior to substance administration. The operation is carried out at least one day prior to the experiment with isofluran anaesthesia and administration of an analgesic (atropin/Rimadyl (3/1) 0.1 ml s.c.). The blood is taken (generally at least 10 time points) within a time window including terminal time points of at least 24 to a maximum of 72 hours after substance administration. When the blood is taken, it is passed into heparinised tubes. Then the blood plasma is obtained by centrifugation and is optionally stored at −20° C. until further processing.

An internal standard (which may also be a chemically unrelated substance) is added to the samples of the compounds according to the invention, calibration samples and qualifiers, and there follows protein precipitation by means of excess acetonitrile. Addition of a buffer solution matched to the LC conditions, and subsequent vortexing, is followed by centrifugation at 1000 g. The supernatant is analysed by LC-MS/MS using C18 or biphenyl reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC (area under the curve), $C_{max}$ (maximal concentration), $t_{1/2}$ (terminal half-life), F (bioavailability), MRT (mean residence time) and CL (clearance), using a validated pharmacokinetic calculation program.

Since the substance quantification is carried out in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixture for 20 min. After centrifugation at 1000 g, the plasma concentration is measured (by means of LC-MS/MS; see above) and determined by calculating the ratio of the whole blood concentration versus plasma concentration ($C_{blood}/C_{plasma}$ value).

B-10. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs, monkeys), and also of human origin, in order to obtain and to compare information about substantially the complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. The liver microsomes and recombinant enzymes were incubated at 37° C. in 50 mM potassium phosphate buffer pH 7.4 with and without Nicotinamide adenine dinucleotide phosphate (NADPH)-generating system consisting of 1 mM $NADP^+$, 10 mM glucose 6-phosphate and 1 unit of glucose 6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%), and the protein was centrifuged off at about 15 000×g. The samples thus stopped were either analysed directly or stored at −20° C. until analysis.

The analysis is carried out by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

B-11. Caco-2 Permeability Test

The permeability of a test substance can be determined with the aid of the Caco-2 cell line, an established in vitro model for permeability predictions at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The CaCo-2 cells (ACC No. 169, DSMZ, Deutsche Sammlung von Mikroorganismen und Zellkulturen, Braunschweig, Germany) are seeded in 24-well plates with inset and cultivated for 14 to 16 days. For the permeability studies, the test substance is dissolved in DMSO and diluted with transport buffer (Hanks Buffered Salt Solution, Gibco/Invitrogen, with 19.9 mM glucose and 9.8 mM HEPES) to the final test concentration. To determine the permeability from the apical to the basolateral side ($P_{app}$A-B) of the test substance, the solution comprising the test substance is placed on the apical side of the Caco-2 cell monolayer, and the transport buffer on the basolateral side. To determine the permeability from the basolateral to the apical side ($P_{app}$B-A) of the test substance, the solution comprising the test substance is placed on the basolateral side of the Caco-2 cell monolayer, and the transport buffer on the apical side. At the start of the experiment, samples are taken from the respective donor compartment to calculate the mass balance afterwards. After a two-hour incubation at 37° C., samples are taken from the two compartments. The samples are analysed by LC-MS/MS, and the apparent permeability coefficients ($P_{app}$) are calculated. For each cell monolayer, the permeability of Lucifer Yellow is determined to ensure cell layer integrity. In each test run, the permeability of atenolol (marker for low permeability) and sulfasalazine (marker for active excretion) is also determined as quality control.

C) Working Examples of Pharmaceutical Compositions

The substances according to the invention can be converted to pharmaceutical preparations as follows:

Tablet:
Composition:
  100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:
  The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:
Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for about 6 h until swelling of the Rhodigel is complete.

Sterile i.v. Solution:

The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

The invention claimed is:

1. A compound of general formula (I)

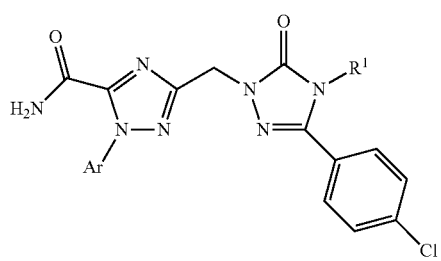

(I)

in which
$R^1$ represents a group of the formula

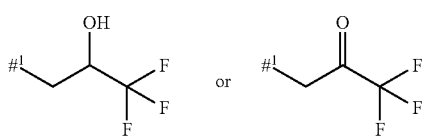

in which
$\#^1$ represents the point of attachment to the nitrogen atom,
Ar represents a group of the formula

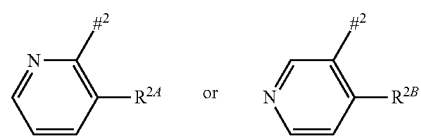

in which
$\#^2$ represents the point of attachment to the nitrogen atom,
$R^{2A}$ represents a group selected from the group consisting of a chlorine atom, a bromine atom, trifluoromethyl, trifluoromethoxy, ethoxycarbonyl, and —C(=O)NH$_2$,
$R^{2B}$ represents a group selected from the group consisting of a chlorine atom, trifluoromethyl, and ethoxycarbonyl;
or a pharmaceutically acceptable salt, hydrate, and/or solvate thereof.

2. A compound of general formula (I) according to claim 1, wherein
$R^1$ represents a group of the formula

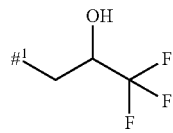

in which
$\#^1$ represents the point of attachment to the nitrogen atom,
Ar represents a group of the formula

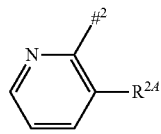

in which
$\#^2$ represents the point of attachment to the nitrogen atom,
$R^{2A}$ represents a group selected from the group consisting of a chlorine atom, a bromine atom, trifluoromethyl, trifluoromethoxy, ethoxycarbonyl, and —C(=O)NH$_2$;
or a pharmaceutically acceptable salt, hydrate, and/or solvate thereof.

3. A compound of general formula (I) according to claim 1, wherein
$R^1$ represents a group of the formula

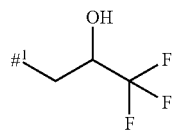

in which
$\#^1$ represents the point of attachment to the nitrogen atom,
Ar represents a group of the formula

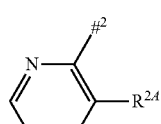

in which

² represents the point of attachment to the nitrogen atom, $R^{2A}$ represents a group selected from the group consisting of a chlorine atom, trifluoromethyl, and trifluoromethoxy;

or a pharmaceutically acceptable salt, hydrate, and/or solvate thereof.

4. A method of preparing a compound of general formula (I) according to claim 1, said method comprising the step of

[A] allowing an intermediate compound of general formula (II):

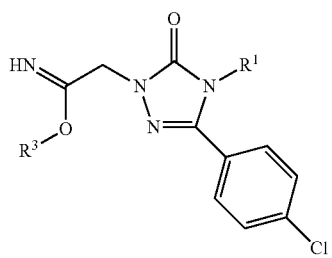

in which $R^1$ is as defined for the compound of general formula (I), $R^3$ represents a $(C_1\text{-}C_4)$-alkyl group, to react in a first step in the presence of a base, and optionally a copper salt, with a compound of general formula (III):

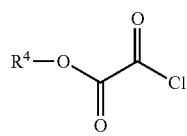

in which $R^4$ represents a $(C_1\text{-}C_4)$-alkyl group, to give an intermediate compound, which is then allowed to react in the presence of a base in a second step with a hydrazine compound of general formula (IV) or a respective salt thereof

in which Ar is as defined for the compound of general formula (I), thereby giving a compound of general formula (V):

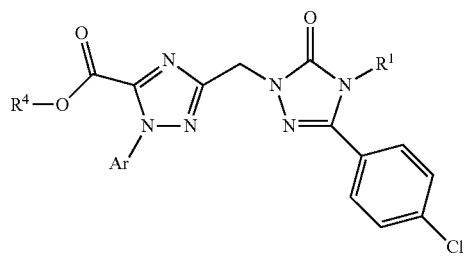

in which $R^1$ and Ar are as defined for the compound of general formula (I), $R^4$ represents a $(C_1\text{-}C_4)$-alkyl group, followed by a subsequent step

[B] allowing the compound of general formula (V) obtained in step [A] to react with ammonia thereby giving a compound of general formula (I):

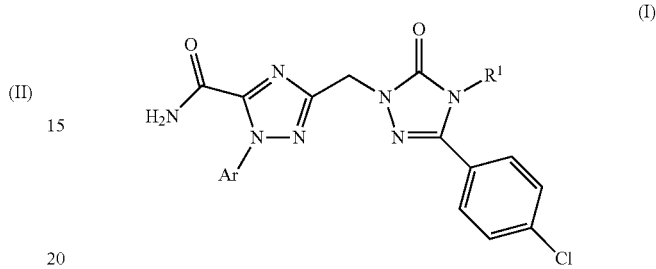

in which $R^1$ and Ar are as defined for the compound of general formula (I), optionally followed by step

[C] converting alcohol of general formula (I-A):

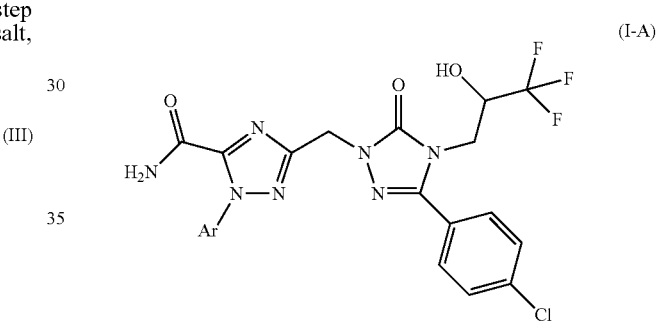

in which Ar is as defined for the compound of general formula (I), to ketone of general formula (I-B):

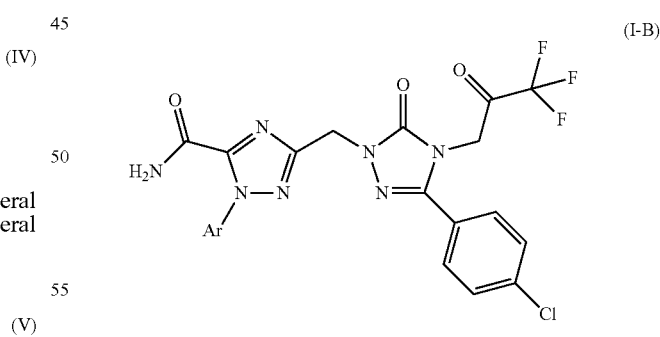

in which Ar is as defined for the compound of general formula (I), by oxidation, each [A], [B] and [C] optionally followed, where appropriate, by (i) separating compounds of general formula (I) thus obtained into their respective enantiomers, and/or (ii) converting compounds of general formula (I) into their respective hydrates, solvates, salts, and/or hydrates or solvates of the salts by treatment with corresponding solvents and/or acids or bases.

5. Compound as defined in claim 1, for use in a method for the treatment of acute kidney disease, chronic kidney disease, acute heart failure, chronic heart failure, preeclampsia, peripheral arterial disease (PAD), coronary microvascular dysfunction (CMD), Raynaud's syndrome and dysmenorrhea.

6. Pharmaceutical composition comprising a compound as defined in claim 1, and one or more pharmaceutically acceptable excipients.

7. Pharmaceutical composition of claim 6, comprising one or more first active ingredients, which are compounds of general formula (I), and one or more further active ingredients, which are one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), antiinflammatory agents, immunosuppressive agents, phosphate binders, and/or compounds which modulate vitamin D metabolism.

8. The pharmaceutical composition as defined in claim 6, for the treatment of acute kidney disease, chronic kidney disease, acute heart failure, chronic heart failure, preeclampsia, peripheral arterial disease (PAD), coronary microvascular dysfunction (CMD), Raynaud's syndrome, and dysmenorrhea.

9. A method for treatment of at least one of the group consisting of acute kidney disease, chronic kidney disease, acute heart failure, chronic heart failure, preeclampsia, peripheral arterial disease (PAD), coronary microvascular dysfunction (CMD), Raynaud's syndrome, and dysmenorrhea in a human or other mammal; comprising administering to the human or other mammal in need thereof a therapeutically effective amount of one or more compounds as defined in claim 1.

10. A method for treatment of at least one of the group consisting of acute kidney disease, chronic kidney disease, acute heart failure, chronic heart failure, preeclampsia, peripheral arterial disease (PAD), coronary microvascular dysfunction (CMD), Raynaud's syndrome, and dysmenorrhea in a human or other mammal; comprising administering to the human or other mammal in need thereof a therapeutically effective amount of a pharmaceutical composition comprising (i) one or more compounds as defined in claim 1, and (ii) one or more pharmaceutically acceptable excipients.

11. Compound as defined in claim 1, for use in a method for the treatment of diabetic nephropathy.

12. The pharmaceutical composition of claim 6, for the treatment of diabetic nephropathy.

13. A method for treatment of diabetic nephropathy in a human or other mammal, comprising administering to the human or other mammal in need thereof a therapeutically effective amount of one or more compounds as defined in claim 1.

14. A method for treatment of diabetic nephropathy in a human or other mammal, comprising administering to the human or other mammal in need thereof a therapeutically effective amount of a pharmaceutical composition comprising (i) one or more compounds as defined in claim 1, and (ii) one or more pharmaceutically acceptable excipients.

* * * * *